(12) United States Patent
Ishigaki et al.

(10) Patent No.: US 10,415,023 B2
(45) Date of Patent: Sep. 17, 2019

(54) MODIFIED LIPASE AND USE THEREOF

(71) Applicant: Amano Enzyme Inc., Nagoya-shi (JP)

(72) Inventors: Yuki Ishigaki, Kakamigahara (JP);
Satoru Ishihara, Kakamigahara (JP);
Shun-ichi Tanaka, Kakamigahara (JP)

(73) Assignee: AMANO ENZYME INC., Nagoya-shi (JP)

( * ) Notice: Subject to any disclaimer, the term of this patent is extended or adjusted under 35 U.S.C. 154(b) by 486 days.

(21) Appl. No.: 15/102,324

(22) PCT Filed: Dec. 8, 2014

(86) PCT No.: PCT/JP2014/082415
§ 371 (c)(1),
(2) Date: Jun. 7, 2016

(87) PCT Pub. No.: WO2015/087833
PCT Pub. Date: Jun. 18, 2015

(65) Prior Publication Data
US 2016/0319259 A1 Nov. 3, 2016

(30) Foreign Application Priority Data
Dec. 10, 2013 (JP) ................................. 2013-255419

(51) Int. Cl.
*C12N 9/20* (2006.01)
*A23L 27/24* (2016.01)
*A23C 9/12* (2006.01)

(52) U.S. Cl.
CPC .............. *C12N 9/20* (2013.01); *A23C 9/1216* (2013.01); *A23L 27/25* (2016.08); *C12Y 301/01003* (2013.01); *A23V 2002/00* (2013.01)

(58) Field of Classification Search
CPC . C12N 9/20; A23C 9/1216; C12Y 301/01003; A23L 27/25; A23V 2002/00
See application file for complete search history.

(56) References Cited

U.S. PATENT DOCUMENTS 7,662,602 B2 * 2/2010 Yaver .................. C12N 9/20
435/193
2004/0001819 A1 1/2004 Bolen et al.

FOREIGN PATENT DOCUMENTS

| JP | 1986-135541 A | 6/1986 |
| JP | 2003-524386 A | 8/2003 |
| JP | 2004-517639 A | 6/2004 |
| JP | 2011-512809 A | 4/2011 |

OTHER PUBLICATIONS

Broun et al., Catalytic plasticity of fatty acid modification enzymes underlying chemical diversity of plant lipids. Science, 1998, vol. 282: 1315-1317. (Year: 1998).*

Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000 ).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for improving enzyme functions. Appl. Biochem. Biotechnol., 2007, vol. 143: (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Guo et al., Protein tolerance to random amino acid change. PNAS., 2004, vol. 101 (25): 9205-9210. (Year: 2004).*
Supplementary European Search Report dated Apr. 25, 2017, issued for the European patent application No. 14869024.1.
Akoh, C. C. et al., "Protein Engineering and Applications of *Candida rugosa* lipase isoforms," Lipids, vol. 39, No. 6, 2004, pp. 513-526.
Longhi, S. et al., "Cloning and nucleotide sequences of two lipase genes from *Candida cylindracea*," Biochim. Biophys. Acta, vol. 1131, 1992, pp. 227-232.
Lotti, M. et al., "Cloning and analysis of *Candida cylindracea* lipase sequences," Gene, vol. 124, 1993, pp. 45-55.
Lee, L.-C. et al., "Altering the Substrate Specificity of *Candida rugosa* LIP4 by Engineering the Substrate-Binding Sites," J. J. Agric. Food Chem., vol. 55, 2007, pp. 5103-5108.
Schmitt, J. et al., "Blocking the tunnel: engineering of *Candida rugosa* lipase mutants with short chain length specificity," Protein Eng., vol. 15, 2002, pp. 595-601.
Lee G.-C et al., "Multiple mutagenesis of non-universal serine codons of the *Candida rugosa LIP2* gene and biochemical characterization of purified recombinant LIP2 lipase overexpressed in *Pichia pastoris*," Biochem. J., vol. 366, 2002, pp. 603-611.
International Search Report dated Jan. 13, 2015, issued for PCT/JP2014/082415.

(Continued)

*Primary Examiner* — Ganapathirama Raghu
(74) *Attorney, Agent, or Firm* — Locke Lord LLP

(57) ABSTRACT

The present invention addresses a problem of providing a lipase derived from a microorganism that is specific for short-chain to medium-chain fatty acids. A modified lipase is obtained by making a substitution in the amino acid sequence of a *Candida cylindracea* derived lipase, wherein the substitution is (1) a substitution of asparagine for an amino acid corresponding to the amino acid at position 428 in the amino acid sequence set forth in SEQ ID NO: 1; or (2) a substitution of phenylalanine, methionine, or isoleucine for an amino acid corresponding to the amino acid at position 429 in the amino acid sequence set forth in SEQ ID NO: 1.

15 Claims, 5 Drawing Sheets
Specification includes a Sequence Listing.

(56) References Cited

OTHER PUBLICATIONS

H. Machida et al., "Industrial production of lipase by microorganisms and its utilization," Japanese Agricultural Science Meeting Magazine (Nippon Nogeikagaku Kaishi), vol. 58, No. 8, 1984, pp. 799-804. (cited in the Mar. 25, 2019 Office Action issued for JP2015-552440).

V.K. Sood et al., "Ripening Changes and Flavor Development in Microbial Enzyme Treated Cheddar Cheese Slurries," Journal of Food Science, 1979, vol. 44, pp. 1690-1694. (cited in the Mar. 25, 2019 Office Action issued for JP2015-552440).

Office Action dated Mar. 25, 2019, issued for the Japanese patent application No. 2015-552440 and English translation thereof.

* cited by examiner

```
                        ....|....|....|....|....|....|....|....|....|....|
                            10         20         30         40         50
LIP1  (SEQ ID NO:2)    APTATLANGD TITGLNAIIN EAFLGIPFAE PPVGNLRFKD PVPYSGSLDG
LIP1' (SEQ ID NO:3)    APTATLANGD TITGLNAIIN EAFLGIPFAE PPVGNLRFKD PVPYSGSLDG
LIP2  (SEQ ID NO:4)    APTATLANGD TITGLNAIVN EKFLGIPFAE PPVGTLRFKP PVPYSASLNG
LIP3  (SEQ ID NO:5)    APTAKLANGD TITGLNAIIN EAFLGIPFAE PPVGNLRFKD PVPYSGSLNG
LIP4  (SEQ ID NO:6)    APTATLANGD TITGLNAIIN EAFLGIPFAQ PPVGNLRFKP PVPYSASLNG
LIP5  (SEQ ID NO:7)    APTATLANGD TITGLNAIIN EAFLGIPFAE PPVGNLRFKD PVPYRGSLNG
Clustal Co             ****.***** ********:* * *******: ****.****  **** .**:*

....|....|....|....|....|....|....|....|....|....|
                            60         70         80         90        100
LIP1                   QKFTSYGPSC MQQNPEGTYE ENLPKAALDL VMQSKVFEAV SPSSEDCLTI
LIP1'                  QKFTSYGPSC MQQNPEGTYE ENLPKAALDL VMQSKVFEAV SPSSEDCLTI
LIP2                   QQFTSYGPSC MQMNPMGSFE DTLPKNARHL VLQSKIFQVV LPNDEDCLTI
LIP3                   QKFTSYGPSC MQQNPEGTFE ENLGKTALDL VMQSKVFQAV LPQSEDCLTI
LIP4                   QKFTSYGPSC MQMNPLGNWD SSLPKAAINS LMQSKLFQAV LPNGEDCLTI
LIP5                   QSFTAYGPSC MQQNPEGTYE ENLPKVALDL VMQSKVFQAV LPNSEDCLTI
Clustal Co             *.**:***** ** ** *.::  .* * * ,  ::***:*:.*  *,.******

....|....|....|....|....|....|....|....|....|....|
                           110        120        130        140        150
LIP1                   NVVRPPGTKA GANLPVMLWI FGGGFEVGGT STFPPAQMIT KSIAMGKPII
LIP1'                  NVVRPPGTKA GANLPVMLWI FGGGFEVGGT STFPPAQMIT KSIAMGKPII
LIP2                   NVIRPPGTRA SAGLPVMLWI FGGGFELGGS SLFPGDQMVA KSVLMGKPVI
LIP3                   NVVRPPGTKA GANLPVMLWI FGGGFEIGSP TIFPPAQMVT KSVLMGKPII
LIP4                   NVVRPSGTKP GANLPVMVWI FGGGFEVGGS SLFPPAQMIT ASVLMGKPII
LIP5                   NVVRPPGTKA GANLPVMLWI FGGGFEIGSP TIFPPAQMVS KSVLMGKPII
Clustal Co             **:**.**:. .*.****:** ******:*.. : ** **::  *: ****:*

....|....|....|....|....|....|....|....|....|....|
                           160        170        180        190        200
LIP1                   HVSVNYRVSS WGFLAGDEIK AEGSANAGLK DQRLGMQWVA DNIAAFGGDP
LIP1'                  HVSVNYRVSS WGFLAGDEIK AEGSANAGLK DQRLGMQWVA DNIAAFGGDP
LIP2                   HVSMNYRVAS WGFLAGPDIQ NEGSGNAGLH DQRLAMQWVA DNIAGFGGDP
LIP3                   HVAVNYRVAS WGFLAGDDIK AEGSGNAGLK DQRLGMQWVA DNIAGFGGDP
LIP4                   HVSMNYRVAS WGFLAGPDIK AEGSGNAGLH DQRLGLQWVA DNIAGFGGDP
LIP5                   HVAVNYRLAS FGFLAGPDIK AEGSSNAGLK DQRLGMQWVA DNIAGFGGDP
Clustal Co             **:***:;* :***** :*: ***.****: ****.**** ****.*****
```

*Fig. 3*

```
                    ....|....|....|....|....|....|....|....|....|....|
                        210        220        230        240        250
LIP1       TKVTIFGESA GSMSVMCHIL WNDGDNTYKG KPLFRAGIMQ SGAMVPSDAV
LIP1'      TKVTIFGESA GSMSVMCHIL WNDGDNTYKG KPLFRAGIMQ SGAMVPSDAV
LIP2       SKVTIYGESA GSMSTFVHLV WNDGDNTYNG KPLFRAAIMQ SGCMVPSDPV
LIP3       SKVTIFGESA GSMSVLCHLI WNDGDNTYKG KPLFRAGIMQ SGAMVPSDPV
LIP4       SKVTIFGESA GSMSVMCQLL WNDGDNTYNG KPLFRAAIMQ SGCMVPSDPV
LIP5       SKVTIFGESA GSMSVLCHLL WNGGDNTYKG KPLFRAGIMQ SGAMVPSDPV
Clustal Co :****:**** ****.: ::: **.*****:* ******.*** **.*****.*

....|....|....|....|....|....|....|....|....|....|
                        260        270        280        290        300
LIP1       DGIYGNEIFD LLASNAGCGS ASDKLACLRG VSSDTLEDAT NNTPGFLAYS
LIP1'      DGIYGNEIFD LLASNAGCGS ASDKLACLRS VSSDTLEDAT NNTPGFLAYS
LIP2       DGTYGTEIYN QVVASAGCGS ASDKLACLRG LSQDTLYQAT SDTPGVLAYP
LIP3       DGTYGNEIYD LFVSSAGCGS ASDKLACLRS ASSDTLLDAT NNTPGFLAYS
LIP4       DGPYGTQIYD QVVASAGCGS ASDKLACLRS ISNDKLFQAT SDTPGALAYP
LIP5       DGTYGTQIYD TLVASTGCSS ASNKLACLRG LSTQALLDAT NDTPGFLSYT
Clustal Co ** **.:*:: ..:.:**.* **:******.  * : * :**  .:*** *:*.

....|....|....|....|....|....|....|....|....|....|
                        310        320        330        340        350
LIP1       SLRLSYLPRP DGVNITDDMY ALVREGKYAN IPVIIGDQND EGTFFGTSSL
LIP1'      SLRLSYLPRP DGVNITDDMY ALVREGKYAN IPVIIGDQND EGTFFGTSSL
LIP2       SLRLSYLPRP DGTFITDDMY ALVRDGKYAH VPVIIGDQND EGTLFGLSSL
LIP3       SLRLSYLPRP DGKNITDDMY KLVRDGKYAS VPVIIGDQND EGTIFGLSSL
LIP4       SLRLSFLPRP DGTFITDDMF KLVRDGKCAN VPVIIGDQND EGTVFALSSL
LIP5       SLRLSYLPRP DGANITDDMY KLVRDGKYAS VPVIIGDQND EGFLFGLSSL
Clustal Co *****:**** **  *****:  ***:** *  :********* ** .*. ***

....|....|....|....|....|....|....|....|....|....|
                        360        370        380        390        400
LIP1       NVTTDAQARE YFKQSFVHAS DAEIDTLMTA YPGDITQGSP FDTGILNALT
LIP1'      NVTTDAQARE YFKQSFVHAS DAEIDTLMTA YPQDITQGSP FDTGILNALT
LIP2       NVTTDAQARA YFKQSFIHAS DAEIDTLMAA YTSDITQGSP FDTGIFNAIT
LIP3       NVTTNAQARA YFKQSFIHAS DAEIDTLMAA YPQDITQGSP FDTGIFNAIT
LIP4       NVTTDAQARQ YFKESFIHAS DAEIDTLMAA YPSDITQGSP FDTGIFNAIT
LIP5       NTTTEADAEA YLRKSFIHAT DADITALKAA YPSDVTQGSP FDTGILNALT
Clustal Co *.**:*:*.  *::::**:**: **:* :* :* *. *:***** *****:**:*
```

*Fig. 4*

```
                  ....|....| ....|....| ....|....| ....|....| ....|....|
                      410        420        430        440        450
     LIP1         PQFKRISAVL GDLGFTLARR YFLNHYTGGT KYSFLSKQLS GLPVLGTFHS
     LIP1'        PQFKRISAVL GDLGFTLARR YFLNHYTGGT KYSFLSKQLS GLPVLGTFHS
     LIP2         PQFKRISALL GDLAFTLARR YFLNYYQGGT KYSFLSKQLS GLPVLGTFHG
     LIP3         PQFKRISAVL GDLAFIHARR YFLNHFQGGT KYSFLSKQLS GLPIMGTFHA
     LIP4         PQFKRIAAVL GDLAFTLPRR YFLNHFQGGT KYSFLSKQLS GLPVIGTHHA
     LIP5         PQLKRINAVL GDLTFTLSRR YFLNHYTGGP KYSFLSKQLS GLPILGTFHA
     Clustal Co   **:*** *:* *** *  .** ****::  **. ********** ***::**.*.

....|....| ....|....| ....|....| ....|....| ....|....|
                      460        470        480        490        500
     LIP1         NDIVFQDYLL GSGSLIYNNA FIAFATDLDP NTAGLLVKWP EYTSSSQSGN
     LIP1'        NDIVFQDYLL GSGSLIYNNA FIAFATDLDP NTAGLLVKWP EYTSSSQSGN
     LIP2         NDIIWQDYLV GSGSVIYNNA FIAFANDLDP NKAGLWTNWP TYTSSSQSGN
     LIP3         NDIVWQDYLL GSGSVIYNNA FIAFATDLDP NTAGLLVNWP KYTSSSQSGN
     LIP4         NDIVWQDFLV SHSSAVYNNA FIAFANDLDP NKAGLLVNWP KYTSSSQSGN
     LIP5         NDIVWQHFLL GSGSVIYNNA FIAFATDLDP NTAGLSVQWP KSTSSSQAGD
     Clustal Co   ***::*.:*: . .* :**** *****.**** *.*** .:**    *****:*:

....|....| ....|....| ....|....| ....
                      510        520        530
     LIP1         NLMMINALGL YTGKDNFRTA GYDALFSNPP SFFV
     LIP1'        NLMMINALGL YTGKDNFRTA GYDALFSNPP SFFV
     LIP2         NLMQINGLGL YTGKDNFRPD AYSALFSNPP SFFV
     LIP3         NLMMINALGL YTGKDNFRTA GYDALMTNPS SFFV
     LIP4         NLLQINALGL YTGKDNFRTA GYDALFTNPS SFFV
     LIP5         NLMQISALGL YTGKDNFRTA GYNALFADPS HFFV
     Clustal Co   **: *..*** ********. .*.**:::*. ***
```

*Fig. 5*

SEQUENCE LISTING

<160> NUMBER OF SEQ ID NOS: 22

<210> SEQ ID NO 1
<211> LENGTH: 549
<212> TYPE: PRT

<213> ORGANISM: Candida cylindracea

<400> SEQUENCE: 1

```
Met Glu Leu Ala Leu Ala Leu Ser Leu Ile Ala Ser Val Ala Ala Ala
1               5                   10                  15

Pro Thr Ala Thr Leu Ala Asn Gly Asp Thr Ile Thr Gly Leu Asn Ala
            20                  25                  30

Ile Ile Asn Glu Ala Phe Leu Gly Ile Pro Phe Ala Glu Pro Pro Val
        35                  40                  45

Gly Asn Leu Arg Phe Lys Asp Pro Val Pro Tyr Ser Gly Ser Leu Asp
    50                  55                  60

Gly Gln Lys Phe Thr Ser Tyr Gly Pro Ser Cys Met Gln Gln Asn Pro
65                  70                  75                  80

Glu Gly Thr Tyr Glu Glu Asn Leu Pro Lys Ala Ala Leu Asp Leu Val
                85                  90                  95

Met Gln Ser Lys Val Phe Glu Ala Val Ser Pro Ser Ser Glu Asp Cys
            100                 105                 110

Leu Thr Ile Asn Val Val Arg Pro Pro Gly Thr Lys Ala Gly Ala Asn
        115                 120                 125

Leu Pro Val Met Leu Trp Ile Phe Gly Gly Phe Glu Val Gly Gly
    130                 135                 140

Thr Ser Thr Phe Pro Pro Ala Gln Met Ile Thr Lys Ser Ile Ala Met
145                 150                 155                 160

Gly Lys Pro Ile Ile His Val Ser Val Asn Tyr Arg Val Ser Ser Trp
                165                 170                 175

Gly Phe Leu Ala Gly Asp Glu Ile Lys Ala Glu Gly Ser Ala Asn Ala
            180                 185                 190

Gly Leu Lys Asp Gln Arg Leu Gly Met Gln Trp Val Ala Asp Asn Ile
        195                 200                 205

Ala Ala Phe Gly Gly Asp Pro Thr Lys Val Thr Ile Phe Gly Glu Ser
    210                 215                 220

Ala Gly Ser Met Ser Val Met Cys His Ile Leu Trp Asn Asp Gly Asp
225                 230                 235                 240

Asn Thr Tyr Lys Gly Lys Pro Leu Phe Arg Ala Gly Ile Met Gln Ser
                245                 250                 255

Gly Ala Met Val Pro Ser Asp Ala Val Asp Gly Ile Tyr Gly Asn Glu
            260                 265                 270

Ile Phe Asp Leu Leu Ala Ser Asn Ala Gly Cys Gly Ser Ala Ser Asp
        275                 280                 285

Lys Leu Ala Cys Leu Arg Gly Val Ser Ser Asp Thr Leu Glu Asp Ala
    290                 295                 300

Thr Asn Asn Thr Pro Gly Phe Leu Ala Tyr Ser Ser Leu Arg Leu Ser
305                 310                 315                 320

Tyr Leu Pro Arg Pro Asp Gly Val Asn Ile Thr Asp Asp Met Tyr Ala
                325                 330                 335

Leu Val Arg Glu Gly Lys Tyr Ala Asn Ile Pro Val Ile Ile Gly Asp
            340                 345                 350

Gln Asn Asp Glu Gly Thr Phe Phe Gly Thr Ser Ser Leu Asn Val Thr
        355                 360                 365

Thr Asp Ala Gln Ala Arg Glu Tyr Phe Lys Gln Ser Phe Val His Ala
    370                 375                 380

Ser Asp Ala Glu Ile Asp Thr Leu Met Thr Ala Tyr Pro Gly Asp Ile
385                 390                 395                 400
```

```
Thr Gln Gly Ser Pro Phe Asp Thr Gly Ile Leu Asn Ala Leu Thr Pro
                405                 410                 415
Gln Phe Lys Arg Ile Ser Ala Val Leu Gly Asp Leu Gly Phe Thr Leu
            420                 425                 430
Ala Arg Arg Tyr Phe Leu Asn His Tyr Thr Gly Gly Thr Lys Tyr Ser
        435                 440                 445
Phe Leu Ser Lys Gln Leu Ser Gly Leu Pro Val Leu Gly Thr Phe His
    450                 455                 460
Ser Asn Asp Ile Val Phe Gln Asp Tyr Leu Leu Gly Ser Gly Ser Leu
465                 470                 475                 480
Ile Tyr Asn Asn Ala Phe Ile Ala Phe Ala Thr Asp Leu Asp Pro Asn
                485                 490                 495
Thr Ala Gly Leu Leu Val Lys Trp Pro Glu Tyr Thr Ser Ser Ser Gln
            500                 505                 510
Ser Gly Asn Asn Leu Met Met Ile Asn Ala Leu Gly Leu Tyr Thr Gly
        515                 520                 525
Lys Asp Asn Phe Arg Thr Ala Gly Tyr Asp Ala Leu Phe Ser Asn Pro
    530                 535                 540
Pro Ser Phe Phe Val
545

<210> SEQ ID NO 2
<211> LENGTH: 534
<212> TYPE: PRT
<213> ORGANISM: Candida cylindracea

<400> SEQUENCE: 2

Ala Pro Thr Ala Thr Leu Ala Asn Gly Asp Thr Ile Thr Gly Leu Asn
1               5                   10                  15
Ala Ile Ile Asn Glu Ala Phe Leu Gly Ile Pro Phe Ala Glu Pro Pro
                20                  25                  30
Val Gly Asn Leu Arg Phe Lys Asp Pro Val Pro Tyr Ser Gly Ser Leu
            35                  40                  45
Asp Gly Gln Lys Phe Thr Ser Tyr Gly Pro Ser Cys Met Gln Gln Asn
    50                  55                  60
Pro Glu Gly Thr Tyr Glu Glu Asn Leu Pro Lys Ala Ala Leu Asp Leu
65                  70                  75                  80
Val Met Gln Ser Lys Val Phe Glu Ala Val Ser Pro Ser Ser Glu Asp
                85                  90                  95
Cys Leu Thr Ile Asn Val Val Arg Pro Pro Gly Thr Lys Ala Gly Ala
            100                 105                 110
Asn Leu Pro Val Met Leu Trp Ile Phe Gly Gly Gly Phe Glu Val Gly
    115                 120                 125
Gly Thr Ser Thr Phe Pro Pro Ala Gln Met Ile Thr Lys Ser Ile Ala
130                 135                 140
Met Gly Lys Pro Ile Ile His Val Ser Val Asn Tyr Arg Val Ser Ser
                145                 150                 155                 160
Trp Gly Phe Leu Ala Gly Asp Glu Ile Lys Ala Glu Gly Ser Ala Asn
                165                 170                 175
Ala Gly Leu Lys Asp Gln Arg Leu Gly Met Gln Trp Val Ala Asp Asn
            180                 185                 190
Ile Ala Ala Phe Gly Gly Asp Pro Thr Lys Val Thr Ile Phe Gly Glu
        195                 200                 205
Ser Ala Gly Ser Met Ser Val Met Cys His Ile Leu Trp Asn Asp Gly
    210                 215                 220
```

```
Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
            245                 250                 255

Glu Ile Phe Asp Leu Leu Ala Ser Asn Ala Gly Cys Gly Ser Ala Ser
            260                 265                 270

Asp Lys Leu Ala Cys Leu Arg Gly Val Ser Ser Asp Thr Leu Glu Asp
        275                 280                 285

Ala Thr Asn Asn Thr Pro Gly Phe Leu Ala Tyr Ser Ser Leu Arg Leu
        290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
        370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Gly Phe Thr
                405                 410                 415

Leu Ala Arg Arg Tyr Phe Leu Asn His Tyr Thr Gly Thr Lys Tyr
            420                 425                 430

Ser Phe Leu Ser Lys Gln Leu Ser Gly Leu Pro Val Leu Gly Thr Phe
            435                 440                 445

His Ser Asn Asp Ile Val Phe Gln Asp Tyr Leu Leu Gly Ser Gly Ser
        450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
        515                 520                 525

Pro Pro Ser Phe Phe Val
    530

<210> SEQ ID NO 3
<211> LENGTH: 534
<212> TYPE: PRT
<213> ORGANISM: Candida cylindracea

<400> SEQUENCE: 3

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
                20                  25                  30

Val Gly Asn Leu Arg Phe Lys Asp Pro Val Pro Tyr Ser Gly Ser Leu
            35                  40                  45

Asp Gly Gln Lys Phe Thr Ser Tyr Gly Pro Ser Cys Met Gln Gln Asn
```

-continued

```
                50                  55                  60
Pro Glu Gly Thr Tyr Glu Asn Leu Pro Lys Ala Ala Leu Asp Leu
 65                  70                  75                  80

Val Met Gln Ser Lys Val Phe Glu Ala Val Ser Pro Ser Ser Glu Asp
                 85                  90                  95

Cys Leu Thr Ile Asn Val Val Arg Pro Gly Thr Lys Ala Gly Ala
                100                 105                 110

Asn Leu Pro Val Met Leu Trp Ile Phe Gly Gly Phe Glu Val Gly
                115                 120                 125

Gly Thr Ser Thr Phe Pro Pro Ala Gln Met Ile Thr Lys Ser Ile Ala
        130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
                180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
        210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
                260                 265                 270

Asp Lys Leu Ala Cys Leu Arg Ser Val Ser Ser Asp Thr Leu Glu Asp
        275                 280                 285

Ala Thr Asn Asn Thr Pro Gly Phe Leu Ala Tyr Ser Ser Leu Arg Leu
        290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
                340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gln Asp
370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Gly Phe Thr
                405                 410                 415

Leu Ala Arg Arg Tyr Phe Leu Asn His Tyr Thr Gly Thr Lys Tyr
                420                 425                 430

Ser Phe Leu Ser Lys Gln Leu Ser Gly Leu Pro Val Leu Gly Thr Phe
        435                 440                 445

His Ser Asn Asp Ile Val Phe Gln Asp Tyr Leu Leu Gly Ser Gly Ser
        450                 455                 460

Leu Ile Tyr Asn Asn Ala Phe Ile Ala Phe Ala Thr Asp Leu Asp Pro
465                 470                 475                 480
```

```
Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
        515                 520                 525

Pro Pro Ser Phe Phe Val
        530

<210> SEQ ID NO 4
<211> LENGTH: 534
<212> TYPE: PRT
<213> ORGANISM: Candida cylindracea

<400> SEQUENCE: 4

Ala Pro Thr Ala Thr Leu Ala Asn Gly Asp Thr Ile Thr Gly Leu Asn
1               5                   10                  15

Ala Ile Val Asn Glu Lys Phe Leu Gly Ile Pro Phe Ala Glu Pro Pro
                20                  25                  30

Val Gly Thr Leu Arg Phe Lys Pro Pro Val Pro Tyr Ser Ala Ser Leu
            35                  40                  45

Asn Gly Gln Gln Phe Thr Ser Tyr Gly Pro Ser Cys Met Gln Met Asn
50                  55                  60

Pro Met Gly Ser Phe Glu Asp Thr Leu Pro Lys Asn Ala Arg His Leu
65                  70                  75                  80

Val Leu Gln Ser Lys Ile Phe Gln Val Val Leu Pro Asn Asp Glu Asp
                85                  90                  95

Cys Leu Thr Ile Asn Val Ile Arg Pro Pro Gly Thr Arg Ala Ser Ala
            100                 105                 110

Gly Leu Pro Val Met Leu Trp Ile Phe Gly Gly Gly Phe Glu Leu Gly
        115                 120                 125

Gly Ser Ser Leu Phe Pro Gly Asp Gln Met Val Ala Lys Ser Val Leu
130                 135                 140

Met Gly Lys Pro Val Ile His Val Ser Met Asn Tyr Arg Val Ala Ser
145                 150                 155                 160

Trp Gly Phe Leu Ala Gly Pro Asp Ile Gln Asn Glu Gly Ser Gly Asn
                165                 170                 175

Ala Gly Leu His Asp Gln Arg Leu Ala Met Gln Trp Val Ala Asp Asn
            180                 185                 190

Ile Ala Gly Phe Gly Gly Asp Pro Ser Lys Val Thr Ile Tyr Gly Glu
        195                 200                 205

Ser Ala Gly Ser Met Ser Thr Phe Val His Leu Val Trp Asn Asp Gly
210                 215                 220

Asp Asn Thr Tyr Asn Gly Lys Pro Leu Phe Arg Ala Ala Ile Met Gln
225                 230                 235                 240

Ser Gly Cys Met Val Pro Ser Asp Pro Val Asp Gly Thr Tyr Gly Thr
                245                 250                 255

Glu Ile Tyr Asn Gln Val Val Ala Ser Ala Gly Cys Gly Ser Ala Ser
            260                 265                 270

Asp Lys Leu Ala Cys Leu Arg Gly Leu Ser Gln Asp Thr Leu Tyr Gln
        275                 280                 285

Ala Thr Ser Asp Thr Pro Gly Val Leu Ala Tyr Pro Ser Leu Arg Leu
290                 295                 300

Ser Tyr Leu Pro Arg Pro Asp Gly Thr Phe Ile Thr Asp Asp Met Tyr
```

```
            305                 310                 315                 320
Ala Leu Val Arg Asp Gly Lys Tyr Ala His Val Pro Val Ile Ile Gly
            325                 330                 335

Asp Gln Asn Asp Glu Gly Thr Leu Phe Gly Leu Ser Ser Leu Asn Val
            340                 345                 350

Thr Thr Asp Ala Gln Ala Arg Ala Tyr Phe Lys Gln Ser Phe Ile His
            355                 360                 365

Ala Ser Asp Ala Glu Ile Asp Thr Leu Met Ala Ala Tyr Thr Ser Asp
            370                 375                 380

Ile Thr Gln Gly Ser Pro Phe Asp Thr Gly Ile Phe Asn Ala Ile Thr
385                 390                 395                 400

Pro Gln Phe Lys Arg Ile Ser Ala Leu Leu Gly Asp Leu Ala Phe Thr
            405                 410                 415

Leu Ala Arg Arg Tyr Phe Leu Asn Tyr Tyr Gln Gly Gly Thr Lys Tyr
            420                 425                 430

Ser Phe Leu Ser Lys Gln Leu Ser Gly Leu Pro Val Leu Gly Thr Phe
            435                 440                 445

His Gly Asn Asp Ile Ile Trp Gln Asp Tyr Leu Val Gly Ser Gly Ser
            450                 455                 460

Val Ile Tyr Asn Asn Ala Phe Ile Ala Phe Ala Asn Asp Leu Asp Pro
465                 470                 475                 480

Asn Lys Ala Gly Leu Trp Thr Asn Trp Pro Thr Tyr Thr Ser Ser Ser
            485                 490                 495

Gln Ser Gly Asn Asn Leu Met Gln Ile Asn Gly Leu Gly Leu Tyr Thr
            500                 505                 510

Gly Lys Asp Asn Phe Arg Pro Asp Ala Tyr Ser Ala Leu Phe Ser Asn
            515                 520                 525

Pro Pro Ser Phe Phe Val
            530

<210> SEQ ID NO 5
<211> LENGTH: 534
<212> TYPE: PRT
<213> ORGANISM: Candida cylindracea

<400> SEQUENCE: 5

Ala Pro Thr Ala Lys Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asn Gly Gln Lys Phe Thr Ser Tyr Gly Pro Ser Cys Met Gln Gln Asn
    50                  55                  60

Pro Glu Gly Thr Phe Glu Glu Asn Leu Gly Lys Thr Ala Leu Asp Leu
65                  70                  75                  80

Val Met Gln Ser Lys Val Phe Gln Ala Val Leu Pro Gln Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Ile Gly
            115                 120                 125

Ser Pro Thr Ile Phe Pro Pro Ala Gln Met Val Thr Lys Ser Val Leu
            130                 135                 140
```

```
Met Gly Lys Pro Ile Ile His Val Ala Val Asn Tyr Arg Val Ala Ser
145                 150                 155                 160

Trp Gly Phe Leu Ala Gly Asp Asp Ile Lys Ala Glu Gly Ser Gly Asn
                165                 170                 175

Ala Gly Leu Lys Asp Gln Arg Leu Gly Met Gln Trp Val Ala Asp Asn
            180                 185                 190

Ile Ala Gly Phe Gly Gly Asp Pro Ser Lys Val Thr Ile Phe Gly Glu
        195                 200                 205

Ser Ala Gly Ser Met Ser Val Leu Cys His Leu Ile Trp Asn Asp Gly
210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Pro Val Asp Gly Thr Tyr Gly Asn
                245                 250                 255

Glu Ile Tyr Asp Leu Phe Val Ser Ser Ala Gly Cys Gly Ser Ala Ser
            260                 265                 270

Asp Lys Leu Ala Cys Leu Arg Ser Ala Ser Ser Asp Thr Leu Leu Asp
        275                 280                 285

Ala Thr Asn Asn Thr Pro Gly Phe Leu Ala Tyr Ser Ser Leu Arg Leu
290                 295                 300

Ser Tyr Leu Pro Arg Pro Asp Gly Lys Asn Ile Thr Asp Asp Met Tyr
305                 310                 315                 320

Lys Leu Val Arg Asp Gly Lys Tyr Ala Ser Val Pro Val Ile Ile Gly
                325                 330                 335

Asp Gln Asn Asp Glu Gly Thr Ile Phe Gly Leu Ser Ser Leu Asn Val
            340                 345                 350

Thr Thr Asn Ala Gln Ala Arg Ala Tyr Phe Lys Gln Ser Phe Ile His
        355                 360                 365

Ala Ser Asp Ala Glu Ile Asp Thr Leu Met Ala Ala Tyr Pro Gln Asp
370                 375                 380

Ile Thr Gln Gly Ser Pro Phe Asp Thr Gly Ile Phe Asn Ala Ile Thr
385                 390                 395                 400

Pro Gln Phe Lys Arg Ile Ser Ala Val Leu Gly Asp Leu Ala Phe Ile
                405                 410                 415

His Ala Arg Arg Tyr Phe Leu Asn His Phe Gln Gly Gly Thr Lys Tyr
            420                 425                 430

Ser Phe Leu Ser Lys Gln Leu Ser Gly Leu Pro Ile Met Gly Thr Phe
        435                 440                 445

His Ala Asn Asp Ile Val Trp Gln Asp Tyr Leu Leu Gly Ser Gly Ser
450                 455                 460

Val Ile Tyr Asn Asn Ala Phe Ile Ala Phe Ala Thr Asp Leu Asp Pro
465                 470                 475                 480

Asn Thr Ala Gly Leu Leu Val Asn Trp Pro Lys Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Met Thr Asn
        515                 520                 525

Pro Ser Ser Phe Phe Val
    530

<210> SEQ ID NO 6
<211> LENGTH: 534
<212> TYPE: PRT
```

<213> ORGANISM: Candida cylindracea

<400> SEQUENCE: 6

```
Ala Pro Thr Ala Thr Leu Ala Asn Gly Asp Thr Ile Thr Gly Leu Asn
1               5                   10                  15
Ala Ile Ile Asn Glu Ala Phe Leu Gly Ile Pro Phe Ala Gln Pro Pro
            20                  25                  30
Val Gly Asn Leu Arg Phe Lys Pro Pro Val Pro Tyr Ser Ala Ser Leu
        35                  40                  45
Asn Gly Gln Lys Phe Thr Ser Tyr Gly Pro Ser Cys Met Gln Met Asn
    50                  55                  60
Pro Leu Gly Asn Trp Asp Ser Ser Leu Pro Lys Ala Ala Ile Asn Ser
65                  70                  75                  80
Leu Met Gln Ser Lys Leu Phe Gln Ala Val Leu Pro Asn Gly Glu Asp
                85                  90                  95
Cys Leu Thr Ile Asn Val Val Arg Pro Ser Gly Thr Lys Pro Gly Ala
            100                 105                 110
Asn Leu Pro Val Met Val Trp Ile Phe Gly Gly Gly Phe Glu Val Gly
        115                 120                 125
Gly Ser Ser Leu Phe Pro Pro Ala Gln Met Ile Thr Ala Ser Val Leu
    130                 135                 140
Met Gly Lys Pro Ile Ile His Val Ser Met Asn Tyr Arg Val Ala Ser
145                 150                 155                 160
Trp Gly Phe Leu Ala Gly Pro Asp Ile Lys Ala Glu Gly Ser Gly Asn
                165                 170                 175
Ala Gly Leu His Asp Gln Arg Leu Gly Leu Gln Trp Val Ala Asp Asn
            180                 185                 190
Ile Ala Gly Phe Gly Gly Asp Pro Ser Lys Val Thr Ile Phe Gly Glu
        195                 200                 205
Ser Ala Gly Ser Met Ser Val Met Cys Gln Leu Leu Trp Asn Asp Gly
    210                 215                 220
Asp Asn Thr Tyr Asn Gly Lys Pro Leu Phe Arg Ala Ala Ile Met Gln
225                 230                 235                 240
Ser Gly Ala Met Val Pro Ser Asp Pro Val Asp Gly Pro Tyr Gly Thr
                245                 250                 255
Gln Ile Tyr Asp Gln Val Val Ala Ser Ala Gly Cys Gly Ser Ala Ser
            260                 265                 270
Asp Lys Leu Ala Cys Leu Arg Ser Ile Ser Asn Asp Lys Leu Phe Gln
        275                 280                 285
Ala Thr Ser Asp Thr Pro Gly Ala Leu Ala Tyr Pro Ser Leu Arg Leu
    290                 295                 300
Ser Phe Leu Pro Arg Pro Asp Gly Thr Phe Ile Thr Asp Asp Met Phe
305                 310                 315                 320
Lys Leu Val Arg Asp Gly Lys Cys Ala Asn Val Pro Val Ile Ile Gly
                325                 330                 335
Asp Gln Asn Asp Glu Gly Thr Val Phe Ala Leu Ser Ser Leu Asn Val
            340                 345                 350
Thr Thr Asp Ala Gln Ala Arg Gln Tyr Phe Lys Glu Ser Phe Ile His
        355                 360                 365
Ala Ser Asp Ala Glu Ile Asp Thr Leu Met Ala Ala Tyr Pro Ser Asp
    370                 375                 380
Ile Thr Gln Gly Ser Pro Phe Asp Thr Gly Ile Phe Asn Ala Ile Thr
385                 390                 395                 400
```

-continued

```
Pro Gln Phe Lys Arg Ile Ala Ala Val Leu Gly Asp Leu Ala Phe Thr
                405                 410                 415

Leu Pro Arg Arg Tyr Phe Leu Asn His Phe Gln Gly Gly Thr Lys Tyr
            420                 425                 430

Ser Phe Leu Ser Lys Gln Leu Ser Gly Leu Pro Val Ile Gly Thr His
        435                 440                 445

His Ala Asn Asp Ile Val Trp Gln Asp Phe Leu Val Ser His Ser Ser
    450                 455                 460

Ala Val Tyr Asn Asn Ala Phe Ile Ala Phe Ala Asn Asp Leu Asp Pro
465                 470                 475                 480

Asn Lys Ala Gly Leu Leu Val Asn Trp Pro Lys Tyr Thr Ser Ser Ser
                485                 490                 495

Gln Ser Gly Asn Asn Leu Leu Gln Ile Asn Ala Leu Gly Leu Tyr Thr
            500                 505                 510

Gly Lys Asp Asn Phe Arg Thr Ala Gly Tyr Asp Ala Leu Phe Thr Asn
        515                 520                 525

Pro Ser Ser Phe Phe Val
    530

<210> SEQ ID NO 7
<211> LENGTH: 534
<212> TYPE: PRT
<213> ORGANISM: Candida cylindracea

<400> SEQUENCE: 7

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Arg Gly Ser Leu
        35                  40                  45

Asn Gly Gln Ser Phe Thr Ala Tyr Gly Pro Ser Cys Met Gln Gln Asn
    50                  55                  60

Pro Glu Gly Thr Tyr Glu Glu Asn Leu Pro Lys Val Ala Leu Asp Leu
65                  70                  75                  80

Val Met Gln Ser Lys Val Phe Gln Ala Val Leu Pro Asn Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Ile Gly
        115                 120                 125

Ser Pro Thr Ile Phe Pro Pro Ala Gln Met Val Ser Lys Ser Val Leu
    130                 135                 140

Met Gly Lys Pro Ile Ile His Val Ala Val Asn Tyr Arg Leu Ala Ser
145                 150                 155                 160

Phe Gly Phe Leu Ala Gly Pro Asp Ile Lys Ala Glu Gly Ser Ser Asn
                165                 170                 175

Ala Gly Leu Lys Asp Gln Arg Leu Gly Met Gln Trp Val Ala Asp Asn
            180                 185                 190

Ile Ala Gly Phe Gly Gly Asp Pro Ser Lys Val Thr Ile Phe Gly Glu
        195                 200                 205

Ser Ala Gly Ser Met Ser Val Leu Cys His Leu Leu Trp Asn Gly Gly
    210                 215                 220

Asp Asn Thr Tyr Lys Gly Lys Pro Leu Phe Arg Ala Gly Ile Met Gln
225                 230                 235                 240
```

```
Ser Gly Ala Met Val Pro Ser Asp Pro Val Asp Gly Thr Tyr Gly Thr
                245                 250                 255

Gln Ile Tyr Asp Thr Leu Val Ala Ser Thr Gly Cys Ser Ser Ala Ser
            260                 265                 270

Asn Lys Leu Ala Cys Leu Arg Gly Leu Ser Thr Gln Ala Leu Leu Asp
        275                 280                 285

Ala Thr Asn Asp Thr Pro Gly Phe Leu Ser Tyr Thr Ser Leu Arg Leu
    290                 295                 300

Ser Tyr Leu Pro Arg Pro Asp Gly Ala Asn Ile Thr Asp Asp Met Tyr
305                 310                 315                 320

Lys Leu Val Arg Asp Gly Lys Tyr Ala Ser Val Pro Val Ile Ile Gly
                325                 330                 335

Asp Gln Asn Asp Glu Gly Phe Leu Phe Gly Leu Ser Ser Leu Asn Thr
            340                 345                 350

Thr Thr Glu Ala Asp Ala Glu Ala Tyr Leu Arg Lys Ser Phe Ile His
        355                 360                 365

Ala Thr Asp Ala Asp Ile Thr Ala Leu Lys Ala Ala Tyr Pro Ser Asp
    370                 375                 380

Val Thr Gln Gly Ser Pro Phe Asp Thr Gly Ile Leu Asn Ala Leu Thr
385                 390                 395                 400

Pro Gln Leu Lys Arg Ile Asn Ala Val Leu Gly Asp Leu Thr Phe Thr
                405                 410                 415

Leu Ser Arg Arg Tyr Phe Leu Asn His Tyr Thr Gly Gly Pro Lys Tyr
            420                 425                 430

Ser Phe Leu Ser Lys Gln Leu Ser Gly Leu Pro Ile Leu Gly Thr Phe
        435                 440                 445

His Ala Asn Asp Ile Val Trp Gln His Phe Leu Leu Gly Ser Gly Ser
    450                 455                 460

Val Ile Tyr Asn Asn Ala Phe Ile Ala Phe Ala Thr Asp Leu Asp Pro
465                 470                 475                 480

Asn Thr Ala Gly Leu Ser Val Gln Trp Pro Lys Ser Thr Ser Ser Ser
                485                 490                 495

Gln Ala Gly Asp Asn Leu Met Gln Ile Ser Ala Leu Gly Leu Tyr Thr
            500                 505                 510

Gly Lys Asp Asn Phe Arg Thr Ala Gly Tyr Asn Ala Leu Phe Ala Asp
        515                 520                 525

Pro Ser His Phe Phe Val
    530

<210> SEQ ID NO 8
<211> LENGTH: 534
<212> TYPE: PRT
<213> ORGANISM: Artificial Sequence
<220> FEATURE:
<223> OTHER INFORMATION: Mutant enzyme 1

<400> SEQUENCE: 8

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asp Gly Gln Lys Phe Thr Ser Tyr Gly Pro Ser Cys Met Gln Gln Asn
    50                  55                  60
```

```
Pro Glu Gly Thr Tyr Glu Glu Asn Leu Pro Lys Ala Ala Leu Asp Leu
 65                  70                  75                  80

Val Met Gln Ser Lys Val Phe Glu Ala Val Ser Pro Ser Ser Glu Asp
                 85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Phe Glu Val Gly
        115                 120                 125

Gly Thr Ser Thr Phe Pro Pro Ala Gln Met Ile Thr Lys Ser Ile Ala
130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
            260                 265                 270

Asp Lys Leu Ala Cys Leu Arg Gly Val Ser Ser Asp Thr Leu Glu Asp
        275                 280                 285

Ala Thr Asn Asn Thr Pro Gly Phe Leu Ala Tyr Ser Ser Leu Arg Leu
290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Asn Gly Phe Thr
                405                 410                 415

Leu Ala Arg Arg Tyr Phe Leu Asn His Tyr Thr Gly Gly Thr Lys Tyr
            420                 425                 430

Ser Phe Leu Ser Lys Gln Leu Ser Gly Leu Pro Val Leu Gly Thr Phe
        435                 440                 445

His Ser Asn Asp Ile Val Phe Gln Asp Tyr Leu Leu Gly Ser Gly Ser
450                 455                 460

Leu Ile Tyr Asn Asn Ala Phe Ile Ala Phe Ala Thr Asp Leu Asp Pro
465                 470                 475                 480
```

```
Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
        515                 520                 525

Pro Pro Ser Phe Phe Val
    530

<210> SEQ ID NO 9
<211> LENGTH: 534
<212> TYPE: PRT
<213> ORGANISM: Artificial Sequence
<220> FEATURE:
<223> OTHER INFORMATION: Mutant enzyme 2

<400> SEQUENCE: 9

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asp Gly Gln Lys Phe Thr Ser Tyr Gly Pro Ser Cys Met Gln Gln Asn
50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Val Gly
        115                 120                 125

Gly Thr Ser Thr Phe Pro Pro Ala Gln Met Ile Thr Lys Ser Ile Ala
130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
            260                 265                 270

Asp Lys Leu Ala Cys Leu Arg Gly Val Ser Ser Asp Thr Leu Glu Asp
        275                 280                 285

Ala Thr Asn Asn Thr Pro Gly Phe Leu Ala Tyr Ser Ser Leu Arg Leu
290                 295                 300
```

```
Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
    370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Phe Phe Thr
                405                 410                 415

Leu Ala Arg Arg Tyr Phe Leu Asn His Tyr Thr Gly Gly Thr Lys Tyr
            420                 425                 430

Ser Phe Leu Ser Lys Gln Leu Ser Gly Leu Pro Val Leu Gly Thr Phe
        435                 440                 445

His Ser Asn Asp Ile Val Phe Gln Asp Tyr Leu Leu Gly Ser Gly Ser
    450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
        515                 520                 525

Pro Pro Ser Phe Phe Val
        530

<210> SEQ ID NO 10
<211> LENGTH: 534
<212> TYPE: PRT
<213> ORGANISM: Artificial Sequence
<220> FEATURE:
<223> OTHER INFORMATION: Mutant enzyme 3

<400> SEQUENCE: 10

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
                20                  25                  30

Val Gly Asn Leu Arg Phe Lys Asp Pro Val Pro Tyr Ser Gly Ser Leu
            35                  40                  45

Asp Gly Gln Lys Phe Thr Ser Tyr Gly Pro Ser Cys Met Gln Gln Asn
    50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Val Gly
        115                 120                 125
```

```
Gly Thr Ser Thr Phe Pro Pro Ala Gln Met Ile Thr Lys Ser Ile Ala
    130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
            260                 265                 270

Asp Lys Leu Ala Cys Leu Arg Gly Val Ser Ser Asp Thr Leu Glu Asp
        275                 280                 285

Ala Thr Asn Asn Thr Pro Gly Phe Leu Ala Tyr Ser Ser Leu Arg Leu
290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Met Phe Thr
                405                 410                 415

Leu Ala Arg Arg Tyr Phe Leu Asn His Tyr Thr Gly Thr Lys Tyr
            420                 425                 430

Ser Phe Leu Ser Lys Gln Leu Ser Gly Leu Pro Val Leu Gly Thr Phe
        435                 440                 445

His Ser Asn Asp Ile Val Phe Gln Asp Tyr Leu Leu Gly Ser Gly Ser
450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
        515                 520                 525

Pro Pro Ser Phe Phe Val
530
```

```
<210> SEQ ID NO 11
<211> LENGTH: 534
<212> TYPE: PRT
<213> ORGANISM: Artificial Sequence
<220> FEATURE:
<223> OTHER INFORMATION: Mutant enzyme 4

<400> SEQUENCE: 11

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asp Gly Gln Lys Phe Thr Ser Tyr Gly Pro Ser Cys Met Gln Gln Asn
    50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Val Gly
        115                 120                 125

Gly Thr Ser Thr Phe Pro Pro Ala Gln Met Ile Thr Lys Ser Ile Ala
    130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
    210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
                245                 250                 255

Glu Ile Phe Asp Leu Leu Ala Ser Asn Ala Gly Cys Gly Ser Ala Ser
            260                 265                 270

Asp Lys Leu Ala Cys Leu Arg Gly Val Ser Ser Asp Thr Leu Glu Asp
        275                 280                 285

Ala Thr Asn Asn Thr Pro Gly Phe Leu Ala Tyr Ser Ser Leu Arg Leu
    290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
```

```
            370               375               380
Ile Thr Gln Gly Ser Pro Phe Asp Thr Gly Ile Leu Asn Ala Leu Thr
385                 390               395                 400

Pro Gln Phe Lys Arg Ile Ser Ala Val Leu Gly Asp Leu Ile Phe Thr
                405               410                 415

Leu Ala Arg Arg Tyr Phe Leu Asn His Tyr Thr Gly Thr Lys Tyr
            420                 425               430

Ser Phe Leu Ser Lys Gln Leu Ser Gly Leu Pro Val Leu Gly Thr Phe
            435                 440               445

His Ser Asn Asp Ile Val Phe Gln Asp Tyr Leu Leu Gly Ser Gly Ser
            450                 455               460

Leu Ile Tyr Asn Asn Ala Phe Ile Ala Phe Ala Thr Asp Leu Asp Pro
465                 470                 475               480

Asn Thr Ala Gly Leu Leu Val Lys Trp Pro Glu Tyr Thr Ser Ser
                485               490                 495

Gln Ser Gly Asn Asn Leu Met Met Ile Asn Ala Leu Gly Leu Tyr Thr
                500               505               510

Gly Lys Asp Asn Phe Arg Thr Ala Gly Tyr Asp Ala Leu Phe Ser Asn
            515                 520               525

Pro Pro Ser Phe Phe Val
            530

<210> SEQ ID NO 12
<211> LENGTH: 1605
<212> TYPE: DNA
<213> ORGANISM: Artificial Sequence
<220> FEATURE:
<223> OTHER INFORMATION: Mutant enzyme 1

<400> SEQUENCE: 12
gcccccaccg ccacgctcgc caacggcgac accatcaccg gtctcaacgc catcatcaac      60
gaggcgttcc tcggcattcc ctttgccgag ccgccggtgg caacctccg cttcaaggac     120
cccgtgccgt actccggctc gctcgatggc agaagttca cgctgtacgg cccgctgtgc      180
atgcagcaga accccgaggg cacctacgag gagaacctcc ccaaggcagc gctcgacttg     240
gtgatgcagt ccaaggtgtt tgaggcggtg ctgccgctga gcgaggactg tctcaccatc     300
aacgtggtgc ggccgccggg caccaaggcg ggtgccaacc tcccggtgat gctctggatc     360
tttgcggcg ggtttgaggt gggtggcacc agcaccttcc ctcccgccca gatgatcacc     420
aagagcattg ccatgggcaa gcccatcatc acgtgagcg tcaactaccg cgtgtcgtcg     480
tgggggttct tggctggcga cgagatcaag gccgagggca gtgccaacgc cggtttgaag     540
gaccagcgct tgggcatgca gtgggtggcg gacaacattg cggcgtttgg cggcgacccg     600
accaaggtga ccatctttgg cgagctggcg ggcagcatgt cggtcatgtg ccacattctc     660
tggaacgacg cgacaacac gtacaagggc aagccgctct ccgcgcgggg catcatgcag     720
ctgggggcca tggtgccgct ggacgccgtg acggcatct acggcaacga gatctttgac     780
ctcttggcgt cgaacgcggg ctgcggcagc gccagcgaca gcttgcgtg cttgcgcggt     840
gtgctgagcg acacgttgga ggacgccacc aacaacaccc ctgggttctt ggcgtactcc     900
tcgttgcggt tgctgtacct ccccggccc gacggcgtga acatcaccga cgacatgtac     960
gccttggtgc gcgagggcaa gtatgccaac atccctgtga tcatcggcga ccagaacgac    1020
gagggcacct tctttggcac cctgctgttg aacgtgacca cggatgccca ggcccgcgag    1080
tacttcaagc agctgtttgt ccacgccagc gacgcggaga tcgacacgtt gatgacggcg    1140
```

```
tacccccggcg acatcaccca gggcctgccg ttcgacacgg gtattctcaa cgccctcacc    1200
ccgcagttca agagaatcct ggcggtgctc ggcgacaacg gctttacgct tgctcgtcgc    1260
tacttcctca accactacac cggcggcacc aagtactcat tcctcctgaa gcagctcctg    1320
ggcttgccgg tgctcggaac gttccactcc aacgacattg tcttccagga ctacttgttg    1380
ggcagcggct cgctcatcta caacaacgcg ttcattgcgt tgccacgga cttggacccc     1440 aacaccgcgg ggttgttggt gaagtggccc gagtacacca gcagcctgca gctgggcaac    1500
aacttgatga tgatcaacgc cttgggcttg tacaccggca aggacaactt ccgcaccgcc    1560
ggctacgacg cgttgttctc caacccgccg ctgttctttg tgtga                    1605

<210> SEQ ID NO 13
<211> LENGTH: 1605
<212> TYPE: DNA
<213> ORGANISM: Artificial Sequence
<220> FEATURE:
<223> OTHER INFORMATION: Mutant enzyme 2

<400> SEQUENCE: 13
gcccccaccg ccacgctcgc caacggcgac accatcaccg gtctcaacgc catcatcaac    60
gaggcgttcc tcggcattcc ctttgccgag ccgccggtgg gcaacctccg cttcaaggac    120
cccgtgccgt actccggctc gctcgatggc cagaagttca cgctgtacgg cccgctgtgc    180
atgcagcaga accccgaggg cacctacgag gagaacctcc ccaaggcagc gctcgacttg    240
gtgatgcagt ccaaggtgtt tgaggcggtg ctgccgctga cgaggactg tctcaccatc     300 aacgtggtgc ggccgccggg caccaaggcg ggtgccaacc tcccggtgat gctctggatc    360
tttggcggcg ggtttgaggt gggtggcacc agcaccttcc ctcccgccca gatgatcacc    420
aagagcattg ccatgggcaa gcccatcatc cacgtgagcg tcaactaccg cgtgtcgtcg    480
tgggggttct tggctggcga cgagatcaag gccgagggca gtgccaacgc cggtttgaag    540
gaccagcgct tgggcatgca gtgggtggcg acaacattg cggcgtttgg cggcgacccg      600
accaaggtga ccatctttgg cgagctggcg ggcagcatgt cggtcatgtg ccacattctc    660
tggaacgacg gcgacaacac gtacaagggc aagccgctct ccgcgcgggg catcatgcag    720 ctggggggcca tggtgccgct ggacgccgtg gacggcatct acggcaacga gatctttgac     780
ctcttggcgt cgaacgcggg ctgcggcagc gccagcgaca agcttgcgtg cttgcgcggt    840
gtgctgagcg acacgttgga ggacgccacc aacaacaccc ctgggttctt ggcgtactcc    900
tcgttgcggt tgctgtacct cccccggccc gacggcgtga acatcaccga cgacatgtac    960
gccttggtgc gcgagggcaa gtatgccaac atccctgtga tcatcggcga ccagaacgac    1020
gagggcacct tctttggcac cctgctgttg aacgtgacca cggatgccca ggcccgcgag    1080
tacttcaagc agctgtttgt ccacgccagc gacgcggaga tcgacacgtt gatgacggcg    1140 tacccccggcg acatcaccca gggcctgccg ttcgacacgg gtattctcaa cgccctcacc    1200
ccgcagttca agagaatcct ggcggtgctc ggcgaccttt tctttacgct tgctcgtcgc    1260
tacttcctca accactacac cggcggcacc aagtactcat tcctcctgaa gcagctcctg    1320
ggcttgccgg tgctcggaac gttccactcc aacgacattg tcttccagga ctacttgttg    1380
ggcagcggct cgctcatcta caacaacgcg ttcattgcgt tgccacgga cttggacccc     1440 aacaccgcgg ggttgttggt gaagtggccc gagtacacca gcagcctgca gctgggcaac    1500
aacttgatga tgatcaacgc cttgggcttg tacaccggca aggacaactt ccgcaccgcc    1560
```
ggctacgacg cgttgttctc caacccgccg ctgttctttg tgtga        1605

<210> SEQ ID NO 14
<211> LENGTH: 1605
<212> TYPE: DNA
<213> ORGANISM: Artificial Sequence
<220> FEATURE:
<223> OTHER INFORMATION: Mutant enzyme 3

<400> SEQUENCE: 14
gcccccaccg ccacgctcgc caacggcgac accatcaccg gtctcaacgc catcatcaac    60
gaggcgttcc tcggcattcc ctttgccgag ccgccggtgg gcaacctccg cttcaaggac   120
cccgtgccgt actccggctc gctcgatggc cagaagttca cgctgtacgg cccgctgtgc   180
atgcagcaga cccccagggg cacctacgag gagaacctcc ccaaggcagc gctcgacttg   240
gtgatgcagt ccaaggtgtt tgaggcggtg ctgccgctga gcgaggactg tctcaccatc   300
aacgtggtgc ggccgccggg caccaaggcg ggtgccaacc tcccggtgat gctctggatc   360
tttggcggcg ggtttgaggt gggtggcacc agcaccttcc ctcccgccca gatgatcacc   420
aagagcattg ccatgggcaa gcccatcatc cacgtgagcg tcaactaccg cgtgtcgtcg   480
tgggggttct tggctggcga cgagatcaag gccgagggca gtgccaacgc cggtttgaag   540
gaccagcgct tgggcatgca gtgggtggcg acaacattg cggcgtttgg cggcgacccg   600
accaaggtga ccatctttgg cgagctggcg ggcagcatgt cggtcatgtg ccacattctc   660
tggaacgacg gcgacaacac gtacaagggc aagccgctct ccgcgcgggg catcatgcag   720
ctgggggcca tggtgccgct ggacgccgtg acggcatct acggcaacga gatctttgac   780
ctcttggcgt cgaacgcggg ctgcggcagc gccagcgaca gcttgcgtg cttgcgcggt   840
gtgctgagcg acacgttgga ggacgccacc aacaacaccc ctgggttctt ggcgtactcc   900
tcgttgcggt tgctgtacct ccccccggcc gacggcgtga acatcaccga cgacatgtac   960
gccttggtgc gcgagggcaa gtatgccaac atccctgtga tcatcggcga ccagaacgac  1020
gagggcacct tctttggcac cctgctgttg aacgtgacca cggatgccca ggcccgcgag  1080
tacttcaagc agctgtttgt ccacgccagc gacgcggaga tcgacacgtt gatgacggcg  1140
taccccggcg acatcaccca gggcctgccg ttcgacacgg tattctcaa cgccctcacc  1200
ccgcagttca agagaatcct ggcggtgctc ggcgacctta tgtttacgct tgctcgtcgc  1260
tacttcctca accactacac cggcggcacc aagtactcat tcctcctgaa gcagctcctg  1320
ggcttgccgg tgctcggaac gttccactcc aacgacattg tcttccagga ctacttgttg  1380
ggcagcggct cgctcatcta caacaacgcg ttcattgcgt ttgccacgga cttggacccc  1440
aacaccgcgg ggttgttggt gaagtggccc gagtacacca gcagcctgca gctgggcaac  1500
aacttgatga tgatcaacgc cttgggcttg tacaccggca aggacaactt ccgcaccgcc  1560
ggctacgacg cgttgttctc caacccgccg ctgttctttg tgtga              1605

<210> SEQ ID NO 15
<211> LENGTH: 1605
<212> TYPE: DNA
<213> ORGANISM: Artificial Sequence
<220> FEATURE:
<223> OTHER INFORMATION: Mutant enzyme 4

<400> SEQUENCE: 15
gcccccaccg ccacgctcgc caacggcgac accatcaccg gtctcaacgc catcatcaac    60
gaggcgttcc tcggcattcc ctttgccgag ccgccggtgg gcaacctccg cttcaaggac   120

```
cccgtgccgt actccggctc gctcgatggc cagaagttca cgctgtacgg cccgctgtgc      180
atgcagcaga accccgaggg cacctacgag gagaacctcc ccaaggcagc gctcgacttg      240
gtgatgcagt ccaaggtgtt tgaggcggtg ctgccgctga gcgaggactg tctcaccatc      300
aacgtggtgc ggccgccggg caccaaggcg ggtgccaacc tcccggtgat gctctggatc      360
tttggcggcg ggtttgaggt gggtggcacc agcaccttcc ctcccgccca gatgatcacc      420
aagagcattg ccatgggcaa gcccatcatc acgtgagcg tcaactaccg cgtgtcgtcg       480
tgggggttct tggctggcga cgagatcaag gccgagggca gtgccaacgc cggtttgaag      540
gaccagcgct tgggcatgca gtgggtggcg gacaacattg cggcgtttgg cggcgacccg      600
accaaggtga ccatctttgg cgagctggcg ggcagcatgt cggtcatgtg ccacattctc      660
tggaacgacg gcgacaacac gtacaagggc aagccgctct tccgcgcggg catcatgcag      720
ctgggggcca tggtgccgct ggacgccgtg gacggcatct acggcaacga gatctttgac      780
ctcttggcgt cgaacgcggg ctgcggcagc gccagcgaca gcttgcgtg cttgcgcggt       840 gtgctgagcg acacgttgga ggacgccacc aacaacaccc ctgggttctt ggcgtactcc      900
tcgttgcggt tgctgtacct cccccggccc gacggcgtga acatcaccga cgacatgtac      960
gccttggtgc gcgagggcaa gtatgccaac atccctgtga tcatcggcga ccagaacgac      1020
gagggcacct tctttggcac cctgctgttg aacgtgacca cggatgccca ggcccgcgag      1080
tacttcaagc agctgtttgt ccacgccagc gacgcggaga tcgacacgtt gatgacggcg      1140
taccccggcg acatcaccca gggcctgccg ttcgacacgg gtattctcaa cgccctcacc      1200
ccgcagttca agagaatcct ggcggtgctc ggcgacctta ttttacgct tgctcgtcgc       1260 tacttcctca accactacac cggcggcacc aagtactcat tcctcctgaa gcagctcctg      1320
ggcttgccgg tgctcggaac gttccactcc aacgacattg tcttccagga ctacttgttg      1380
ggcagcggct cgctcatcta caacaacgcg ttcattgcgt ttgccacgga cttggacccc     1440
aacaccgcgg ggttgttggt gaagtggccc gagtacacca gcagcctgca gctgggcaac     1500
aacttgatga tgatcaacgc cttgggcttg tacaccggca aggacaactt ccgcaccgcc      1560
ggctacgacg cgttgttctc caacccgccg ctgttctttg tgtga                     1605
```

<210> SEQ ID NO 16
<211> LENGTH: 1605
<212> TYPE: DNA
<213> ORGANISM: Artificial Sequence
<220> FEATURE:
<223> OTHER INFORMATION: Mutant enzyme 1

<400> SEQUENCE: 16

```
gcccccaccg ccacgctcgc caacggcgac accatcaccg gtctcaacgc catcatcaac       60
gaggcgttcc tcggcattcc cttttgccgag ccgccggtgg gcaacctccg cttcaaggac      120
cccgtgccgt actccggctc gctcgatggc cagaagttca cgtcttacgg cccgtcttgc      180
atgcagcaga accccgaggg cacctacgag gagaacctcc ccaaggcagc gctcgacttg      240
gtgatgcagt ccaaggtgtt tgaggcggtg tctccgtcta gcgaggactg tctcaccatc      300
aacgtggtgc ggccgccggg caccaaggcg ggtgccaacc tcccggtgat gctctggatc      360
tttggcggcg ggtttgaggt gggtggcacc agcaccttcc ctcccgccca gatgatcacc      420
aagagcattg ccatgggcaa gcccatcatc acgtgagcg tcaactaccg cgtgtcgtcg       480
tgggggttct tggctggcga cgagatcaag gccgagggca gtgccaacgc cggtttgaag      540
```

```
gaccagcgct tgggcatgca gtgggtggcg acaacattg cggcgtttgg cggcgacccg       600
accaaggtga ccatctttgg cgagtctgcg ggcagcatgt cggtcatgtg ccacattctc       660
tggaacgacg gcgacaacac gtacaagggc aagccgctct ccgcgcggg catcatgcag        720 tctggggcca tggtgccgtc tgacgccgtg acggcatcc acggcaacga gatctttgac        780
ctcttggcgt cgaacgcggg ctgcggcagc gccagcgaca agcttgcgtg cttgcgcggt      840
gtgtctagcg acacgttgga ggacgccacc aacaacaccc ctgggttctt ggcgtactcc      900
tcgttgcggt tgtcttacct cccccggccc gacggcgtga acatcaccga cgacatgtac      960
gccttggtgc gcgagggcaa gtatgccaac atccctgtga tcatcggcga ccagaacgac     1020
gagggcacct tctttggcac ctcttctttg aacgtgacca cggatgccca ggcccgcgag     1080
tacttcaagc agtcttttgt ccacgccagc gacgcggaga tcgacacgtt gatgacggcg     1140
taccccggcg acatcaccca gggctctccg ttcgacacgg gtattctcaa cgccctcacc     1200
ccgcagttca agagaatctc tgcggtgctc ggcgacaacg gctttacgct tgctcgtcgc     1260
tacttcctca accactacac cggcggcacc aagtactcat tcctctctaa gcagctctct     1320
ggcttgccgg tgctcggaac gttccactcc aacgacattg tcttccagga ctacttgttg     1380
ggcagcggct cgctcatcta caacaacgcg ttcattgcgt ttgccacgga cttggacccc     1440
aacaccgcgg ggttgttggt gaagtggccc gagtacacca gcagctctca gtctggcaac     1500
aacttgatga tgatcaacgc cttgggcttg tacaccggca aggacaactt ccgcaccgcc     1560
ggctacgacg cgttgttctc caacccgccg tctttctttg tgtga                     1605

<210> SEQ ID NO 17
<211> LENGTH: 1605
<212> TYPE: DNA
<213> ORGANISM: Artificial Sequence
<220> FEATURE:
<223> OTHER INFORMATION: Mutant enzyme 2

<400> SEQUENCE: 17
gcccccaccg ccacgctcgc caacggcgac accatcaccg gtctcaacgc catcatcaac        60
gaggcgttcc tcggcattcc cttttgccgag ccgccggtgg gcaacctccg cttcaaggac      120
cccgtgccgt actccggctc gctcgatggc cagaagttca cgtcttacgg cccgtcttgc       180
atgcagcaga acccccgaggg cacctacgag gagaacctcc ccaaggcagc gctcgacttg      240
gtgatgcagt ccaaggtgtt tgaggcggtg tctccgtcta gcgaggactg tctccaccatc     300 aacgtggtgc ggccgccggg caccaaggcg ggtgccaacc tcccggtgat gctctggatc      360
tttggcggcg ggtttgaggt gggtggcacc agcaccttcc ctcccgccca gatgatcacc      420
aagagcattg ccatgggcaa gcccatcatc cacgtgagcg tcaactaccg cgtgtcgtcg      480
tgggggttct tggctggcga cgagatcaag gccgagggca gtgccaacgc cggtttgaag      540
gaccagcgct tgggcatgca gtgggtggcg acaacattg cggcgtttgg cggcgacccg       600
accaaggtga ccatctttgg cgagtctgcg ggcagcatgt cggtcatgtg ccacattctc       660
tggaacgacg gcgacaacac gtacaagggc aagccgctct ccgcgcggg catcatgcag        720 tctggggcca tggtgccgtc tgacgccgtg acggcatcc acggcaacga gatctttgac        780
ctcttggcgt cgaacgcggg ctgcggcagc gccagcgaca agcttgcgtg cttgcgcggt      840
gtgtctagcg acacgttgga ggacgccacc aacaacaccc ctgggttctt ggcgtactcc      900
tcgttgcggt tgtcttacct cccccggccc gacggcgtga acatcaccga cgacatgtac      960
gccttggtgc gcgagggcaa gtatgccaac atccctgtga tcatcggcga ccagaacgac     1020
```

```
gagggcacct tctttggcac ctcttctttg aacgtgacca cggatgccca ggcccgcgag    1080
tacttcaagc agtcttttgt ccacgccagc gacgcggaga tcgacacgtt gatgacggcg    1140
taccccggcg acatcaccca gggctctccg ttcgacacgg gtattctcaa cgccctcacc    1200
ccgcagttca agagaatctc tgcggtgctc ggcgaccttt tctttacgct tgctcgtcgc    1260
tacttcctca accactacac cggcggcacc aagtactcat tcctctctaa gcagctctct    1320
ggcttgccgg tgctcggaac gttccactcc aacgacattg tcttccagga ctacttgttg    1380
ggcagcggct cgctcatcta caacaacgcg ttcattgcgt ttgccacgga cttggacccc    1440
aacaccgcgg ggttgttggt gaagtggccc gagtacacca gcagctctca gtctggcaac    1500
aacttgatga tgatcaacgc cttgggcttg tacaccggca aggacaactt ccgcaccgcc    1560
ggctacgacg cgttgttctc caacccgccg tctttctttg tgtga                   1605

<210> SEQ ID NO 18
<211> LENGTH: 1605
<212> TYPE: DNA
<213> ORGANISM: Artificial Sequence
<220> FEATURE:
<223> OTHER INFORMATION: Mutant enzyme 3

<400> SEQUENCE: 18
gcccccaccg ccacgctcgc caacggcgac accatcaccg gtctcaacgc catcatcaac      60
gaggcgttcc tcggcattcc cttttgccgag ccgccggtgg gcaacctccg cttcaaggac    120
cccgtgccgt actccggctc gctcgatggc cagaagttca cgtcttacgg cccgtcttgc    180
atgcagcaga ccccgagggg cacctacgag gagaacctcc ccaaggcagc gctcgacttg    240
gtgatgcagt ccaaggtgtt tgaggcggtg tctccgtcta gcgaggactg tctcaccatc    300
aacgtggtgc ggccgccggg caccaaggcg ggtgccaacc tcccggtgat gctctggatc    360
tttggcggcg ggtttgaggt gggtggcacc agcaccttcc ctcccgccca gatgatcacc    420
aagagcattg ccatgggcaa gcccatcatc cacgtgagcg tcaactaccg cgtgtcgtcg    480
tgggggttct ggctggcga cgagatcaag gccgagggca gtgccaacgc cggtttgaag    540
gaccagcgct tgggcatgca gtgggtggcg acaacattg cggcgtttgg cggcgacccg    600
accaaggtga ccatctttgg cgagtctgcg ggcagcatgt cggtcatgtg ccacattctc    660
tggaacgacg gcgacaacac gtacaagggc aagccgctct tccgcgcggg catcatgcag    720
tctggggcca tggtgccgtc tgacgccgtg acggcatct acggcaacga gatctttgac    780
ctcttggcgt cgaacgcggg ctgcggcagc gccagcgaca gcttgcgtg cttgcgcggt    840 gtgtctagcg acacgttgga ggacgccacc aacaacaccc ctgggttctt ggcgtactcc    900
tcgttgcggt tgtcttacct ccccccggcc gacgcgtga acatcaccga cgacatgtac    960
gccttggtgc gcgagggcaa gtatgccaac atccctgtga tcatcggcga ccagaacgac    1020
gagggcacct tctttggcac ctcttctttg aacgtgacca cggatgccca ggcccgcgag    1080
tacttcaagc agtcttttgt ccacgccagc gacgcggaga tcgacacgtt gatgacggcg    1140
taccccggcg acatcaccca gggctctccg ttcgacacgg gtattctcaa cgccctcacc    1200
ccgcagttca agagaatctc tgcggtgctc ggcgacctta tgtttacgct tgctcgtcgc    1260
tacttcctca accactacac cggcggcacc aagtactcat tcctctctaa gcagctctct    1320
ggcttgccgg tgctcggaac gttccactcc aacgacattg tcttccagga ctacttgttg    1380
ggcagcggct cgctcatcta caacaacgcg ttcattgcgt ttgccacgga cttggacccc    1440
```

```
aacaccgcgg ggttgttggt gaagtggccc gagtacacca gcagctctca gtctggcaac   1500
aacttgatga tgatcaacgc cttgggcttg tacaccggca aggacaactt ccgcaccgcc   1560
ggctacgacg cgttgttctc caacccgccg tctttctttg tgtga                  1605

<210> SEQ ID NO 19
<211> LENGTH: 1605
<212> TYPE: DNA
<213> ORGANISM: Artificial Sequence
<220> FEATURE:
<223> OTHER INFORMATION: Mutant enzyme 4

<400> SEQUENCE: 19
gcccccaccg ccacgctcgc caacggcgac accatcaccg gtctcaacgc catcatcaac     60
gaggcgttcc tcggcattcc ctttgccgag ccgccggtgg gcaacctccg cttcaaggac    120
cccgtgccgt actccggctc gctcgatggc cagaagttca cgtcttacgg cccgtcttgc    180
atgcagcaga accccgaggg cacctacgag gagaacctcc ccaaggcagc gctcgacttg    240
gtgatgcagt ccaaggtgtt tgaggcggtg tctccgtcta gcgaggactg tctccaccat    300
aacgtggtgc ggccgccggg caccaaggcg ggtgccaacc tcccggtgat gctctggatc    360
tttggcggcg ggtttgaggt gggtggcacc agcaccttcc ctcccgccca gatgatcacc    420
aagagcattg ccatgggcaa gcccatcatc cacgtgagcg tcaactaccg cgtgtcgtcg    480
tgggggttct tggctggcga cgagatcaag gccgagggca gtgccaacgc cggtttgaag    540
gaccagcgct gggcatgcca gtgggtggcg gacaacattg cggcgtttgg cggcgacccg    600
accaaggtga ccatctttgg cgagtctgcg ggcagcatgt cggtcatgtg ccacattctc    660
tggaacgacg gcgacaacac gtacaagggc aagccgctct ccgcgcgggg catcatgcag    720 tctgggggcca tggtgccgtc tgacgccgtg acggcatct acggcaacga gatctttgac    780
ctcttggcgt cgaacgcggg ctgcggcagc gccagcgaca gcttgcgtg cttgcgcggt    840 gtgtctagcg acacgttgga ggacgccacc aacaacaccc ctgggttctt ggcgtactcc    900
tcgttgcggt tgtcttacct ccccccggcc gacggcgtga acatcaccga cgacatgtac    960
gccttggtgc gcgagggcaa gtatgccaac atccctgtga tcatcggcga ccagaacgac   1020
gagggcacct tctttggcac ctcttctttg aacgtgacca cggatgccca ggcccgcgag   1080
tacttcaagc agtcttttgt ccacgccagc gacgcggaga tcgacacgtt gatgacggcg   1140
taccccggcg acatcaccca gggctctccg ttcgacacgg gtattctcaa cgccctcacc   1200
ccgcagttca agagaatctc tgcggtgctc ggcgaccta tgtttacgct tgctcgtcgc   1260
tacttcctca accactacac cggcggcacc aagtactcat tcctctctaa gcagctctct   1320
ggcttgccgg tgctcggaac gttccactcc aacgacattg tcttccagga ctacttgttg   1380
ggcagcggct cgctcatcta caacaacgcg ttcattgcgt ttgccacgga cttggacccc   1440
aacaccgcgg ggttgttggt gaagtggccc gagtacacca gcagctctca gtctggcaac   1500
aacttgatga tgatcaacgc cttgggcttg tacaccggca aggacaactt ccgcaccgcc   1560
ggctacgacg cgttgttctc caacccgccg tctttctttg tgtga                  1605

<210> SEQ ID NO 20
<211> LENGTH: 1650
<212> TYPE: DNA
<213> ORGANISM: Candida cylindracea

<400> SEQUENCE: 20
atggagctcg ctcttgcgct cctgctcatt gcctcggtgg ctgctgcccc caccgccacg    60
```

```
ctcgccaacg gcgacaccat caccggtctc aacgccatca tcaacgaggc gttcctcggc        120
attccctttg ccgagccgcc ggtgggcaac ctccgcttca aggaccccgt gccgtactcc        180
ggctcgctcg atggccagaa gttcacgctg tacggcccgc tgtgcatgca gcagaacccc        240
gagggcacct acgaggagaa cctccccaag gcagcgctcg acttggtgat gcagtccaag        300
gtgtttgagg cggtgctgcc gctgagcgag gactgtctca ccatcaacgt ggtgcggccg        360
ccgggcacca aggcgggtgc caacctcccg gtgatgctct ggatctttgg cggcgggttt        420
gaggtgggtg gcaccagcac cttccctccc gcccagatga tcaccaagag cattgccatg        480
ggcaagccca tcatccacgt gagcgtcaac taccgcgtgt cgtcgtgggg gttcttggct        540
ggcgacgaga tcaaggccga gggcagtgcc aacgccggtt tgaaggacca gcgcttgggc        600
atgcagtggg tggcggacaa cattgcggcg tttgcggcg acccgaccaa ggtgaccatc        660
tttggcgagc tggcgggcag catgtcggtc atgtgccaca ttctctggaa cgacggcgac        720
aacacgtaca agggcaagcc gctcttccgc gcgggcatca tgcagctggg ggccatggtg        780
ccgctggacg ccgtggacgg catctacggc aacgagatct tgacctcttt ggcgtcgaac        840
gcgggctgcg gcagcgccag cgacaagctt gcgtgcttgc gcggtgtgct gagcgacacg        900
ttggaggacg ccaccaacaa caccccctggg ttcttggcgt actcctcgtt gcggttgctg       960
tacctccccc ggcccgacgg cgtgaacatc ccgacgacga tgtacgcctt ggtgcgcgag       1020
ggcaagtatg ccaacatccc tgtgatcatc ggcgaccaga cgacgagggg cacctctctt       1080
ggcaccctgc tgttgaacgt gaccacggat gcccaggccc gcgagtactt caagcagctg       1140
tttgtccacg ccagcgacgc ggagatcgac acgttgatga cggcgtaccc cggcgacatc       1200
acccagggcc tgccgttcga cacgggtatt ctcaacgccc tcaccccgca gttcaagaga       1260
atcctggcgg tgctcggcga ccttggcttt acgcttgctc gtcgctactt cctcaaccac       1320
tacaccggcg gcaccaagta ctcattcctc ctgaagcagc tcctgggctt gccggtgctc       1380
ggaacgttcc actccaacga cattgtcttc caggactact tgttgggcag cggctcgctc       1440
atctacaaca acgcgttcat tgcgtttgcc acggacttgg accccaacac cgcggggttg       1500
ttggtgaagt ggcccgagta caccagcagc ctgcagctgg gcaacaactt gatgatgatc       1560
aacgccttgg gcttgtacac cggcaaggac aacttccgca ccgccggcta cgacgcgttg       1620
ttctccaacc cgccgctgtt cttgtgtga                                         1650

<210> SEQ ID NO 21
<211> LENGTH: 45
<212> TYPE: DNA
<213> ORGANISM: Candida cylindracea

<400> SEQUENCE: 21
atggagctcg ctcttgcgct cctgctcatt gcctcggtgg ctgct                       45

<210> SEQ ID NO 22
<211> LENGTH: 15
<212> TYPE: PRT
<213> ORGANISM: Candida cylindracea

<400> SEQUENCE: 22

Met Glu Leu Ala Leu Ala Leu Ser Leu Ile Ala Ser Val Ala Ala
1               5                   10                  15
```

MODIFIED LIPASE AND USE THEREOF

TECHNICAL FIELD

The present invention relates to a modified lipase. Specifically, the present invention provides, for example, a modified lipase and a method for producing dairy products using such a modified lipase. The present application claims priority from Japanese Patent Application No. 2013-255419, filed on Dec. 10, 2013, the entire content of which is incorporated by reference.

BACKGROUND ART

Lipases have been used for formation and enhancement of the flavor of dairy products. Traditionally, there have been used preparations of lipases from kids, calves, or lambs. These ruminant lipases have a specificity that short-chain fatty acids ($C_4$ and $C_6$ fatty acids) are released from milk fat, and are suitable for the formation of the flavor of dairy products.

However, there is a strong industrial need for an alternative to animal-derived lipases because kosher or halal qualities are required for enzyme preparations utilized for food processing. To meet the need, proposals have been made, for example, to use microbial enzymes (for example, Patent Document 1) and recombinant enzymes (for example, Patent Document 2). In addition, attempts have also been made to modify lipases by genetic engineering, for application to particular purposes (for example, Patent Documents 3 to 5).

CITATIONS LIST

Patent Literatures

Patent Literature 1: JP 61-135541 A
Patent Literature 2: US 2004/0001819
Patent Literature 3: JP 2011-512809
Patent Literature 4: JP 2003-524386
Patent Literature 5: JP 2004-517639

Non Patent Literature

Non Patent Literature 1: J. Schmitt et al., Protein Engineering, vol. 15, no. 7, pp. 595-601, 2002

SUMMARY OF INVENTION

Technical Problems

Microbial lipases are more specific for long-chain fatty acids than for short-chain fatty acids, and thus their action on milk fat will give a profile that many of the fatty acids released from the milk fat have a long chain. Long-chain fatty acids, which are responsible for soap odor, are not favorable as the favor of dairy products, particularly of cheeses.

Under this background, the present invention addresses a problem of providing a lipase derived from a microorganism that is specific for short-chain to medium-chain fatty acids, and a use of such a lipase.

Solutions to Problems

In the course of the investigation to solve the above-mentioned problem, the inventors focused on a *Candida cylindracea* derived lipase (a lipase formerly referred to as a *Candida rugosa* derived lipase was used) and attempted its modification. After trial and error, the inventors succeeded in finding very useful mutation sites that can lead to the achievement of the goals of the present invention, from the amino acids which form the substrate pocket. Variants with a given amino acid substitution made at each of these mutation sites hydrolyzed milk fat so that short-chain to medium-chain fatty acids ($C_4$ to $C_8$ fatty acids) were selectively released as in the case of an animal lipase. These variants worked well on short-chain fatty acids ($C_4$ to $C_6$ fatty acids), and best on $C_4$ fatty acid. As just mentioned, the inventors succeeded, as a result of these amino acid mutations, in bringing the substrate specificities of lipases close to that of the animal lipase. In connection with this, for the *Candida cylindracea* derived lipase, there have been reported mutations (amino acid substitutions) considered to be effective for its substrate specificity (Non-Patent Document 1), but it was observed that the newly found mutations were more effective in modifying the substrate specificity (specificity for short-chain fatty acids).

In present invention, it is likely that mutagenesis procedures similar to those as described herein can also be applied to other enzymes having a high degree of amino acid sequence identity relative to LIP1 used in Examples, in light of common general technical knowledge that enzymes having a high degree of amino acid sequence identity (typically isozymes) have a high degree of similarity in their three-dimensional structure, particularly in sites involved in their activity, such as active site and substrate pocket, and that it is highly probable that a similar mutation in such enzymes gives rise to a similar effect.

The inventions described below are based mainly on the above-described results and observation.

[1] A modified lipase consisting of an amino acid sequence with a substitution made in the amino acid sequence of a *Candida cylindracea* derived lipase, wherein the substitution is:

(1) a substitution of asparagine for an amino acid corresponding to the amino acid at position 428 in the amino acid sequence set forth in SEQ ID NO: 1; or (2) a substitution of phenylalanine, methionine, or isoleucine for an amino acid corresponding to the amino acid at position 429 in the amino acid sequence set forth in SEQ ID NO: 1.

[2] The modified lipase according to [1], wherein the amino acid sequence of the *Candida cylindracea* derived lipase is an amino acid sequence that is 70% or more identical to the amino acid sequence of SEQ ID NO: 2 and wherein the substitution is the substitution represented in (1).

[3] The modified lipase according to [1], wherein the amino acid sequence of the *Candida cylindracea* derived lipase is an amino acid sequence that is 90% or more identical to the amino acid sequence of SEQ ID NO: 2 and wherein the substitution is the substitution represented in (2).

[4] The modified lipase according to [2] or [3], wherein the amino acid sequence of the *Candida cylindracea* derived lipase is an amino acid sequence of any one of SEQ ID NOs: 2 to 7.

[5] The modified lipase according to [1], consisting of the amino sequence set forth in any one of SEQ ID NOs: 8 to 11.

[6] A gene encoding the modified lipase according to any one of [1] to [5].

[7] The gene according to [6], comprising the base sequence set forth in any one of SEQ ID NOs: 12 to 19.

[8] A recombinant DNA comprising the gene according to [6] or [7].

[9] A microorganism carrying the recombinant DNA according to [8].

[10] The microorganism according to [9], wherein the host is *Escherichia coli*, *Candida cylindracea*, *Aspergillus oryzae*, *Bacillus subtilis*, or *Pichia pastoris*.

[11] An enzyme preparation comprising the modified lipase according to any one of [1] to [5].

[12] A method for improving the flavor of a food product or food raw material, characterized in that the enzyme according to any one of [1] to [5] or the enzyme preparation according to [11] is allowed to act on the food product or food raw material.

[13] A method for producing a food product, characterized in that the enzyme according to any one of [1] to [5] or the enzyme preparation according to [11] is allowed to act on a food raw material or intermediate product.

[14] The method according to [12] or [13], wherein the food product is a dairy product.

[15] A flavor-improving agent that is allowed to act on a food product or food raw material, comprising the enzyme according to any one of [1] to [5] or the enzyme preparation according to [11].

[16] A food product or food raw material obtained by treatment with the enzyme according to any one of [1] to [5] or the enzyme preparation according to [11].

BRIEF DESCRIPTION OF DRAWINGS

FIG. 3 shows a comparison of the sequences of *Candida cylindracea* derived wild-type lipases LIP1 (SEQ ID NO: 2), LIP1' (SEQ ID NO: 3), LIP2 (SEQ ID NO: 4), LIP3 (SEQ ID NO: 5), LIP4 (SEQ ID NO: 6), and LIP5 (SEQ ID NO: 7).

FIG. 4 is a continuation of FIG. 3.

FIG. 5 is a continuation of FIG. 4.

DESCRIPTION OF EMBODIMENTS

Figure 1:
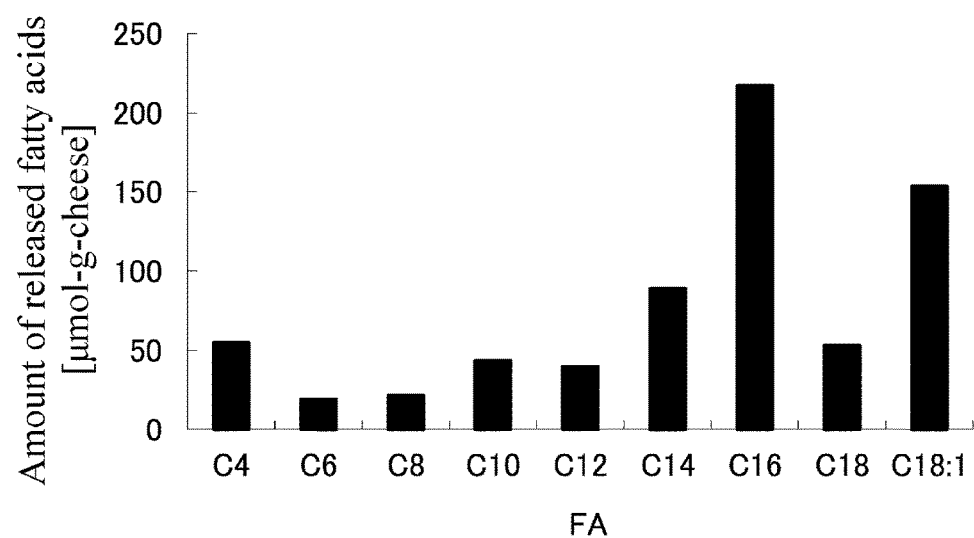
FIG. 1 shows the composition of released fatty acids after treatment with a wild-type enzyme. A *Candida cylindracea* derived wild-type lipase LIP1 was allowed to act on cheese (used as a substrate) and the composition of the released fatty acids was analyzed.

For convenience of description, some of the terms used in relation to the present invention are defined as follows.
(Terminology)

The term "modified lipase" refers to an enzyme obtained by modification or mutation of a particular lipase (which is referred to as a "reference lipase" for convenience of description). The reference lipase is a *Candida cylindracea* derived lipase or a *Candida rugosa* derived lipase. The terms "*Candida cylindracea* derived lipase" and "*Candida rugosa* derived lipase" are used interchangeably.

The term "*Candida cylindracea* derived lipase" is a lipase that is obtained from a strain of *Candida cylindracea* as the source, and includes lipases produced by *Candida cylindracea*, lipases produced by mutated strains of *Candida cylindracea* (variant strains), lipases expressed, for example, in other microorganism, using the genetic information of such enzymes, or the like. Similarly, the term "*Candida rugosa* derived lipase" is a lipase that is obtained from a strain of *Candida rugosa* as the source, and includes lipases produced by *Candida rugosa*, lipases produced by mutated strains of *Candida rugosa* (variant strains), lipases expressed, for example, in other microorganism, using the genetic information of such enzymes, or the like.

In the present invention, an "amino acid substitution" is carried out as modification or mutation. Therefore, some amino acid residues are found to be different when a modified lipase and the reference lipase therefor are compared. In the specification, a modified lipase is also referred to as a modified enzyme or as a variant.

In the specification, amino acids are designated according to the common practice, as their single letters as described below:

methionine: M; serine: S; alanine: A; threonine: T; valine: V; tyrosine: Y; leucine: L; asparagine: N; isoleucine: I; glutamine: Q; proline: P; aspartic acid: D; phenylalanine: F; glutamic acid: E; tryptophan: W; lysine: K; cysteine: C; arginine: R; glycine: G; and histidine: H.

In the specification, the positions of amino acids in an amino acid sequence are specified by assigning the numbers from the N-terminus toward the C-terminus of the amino acid sequence, wherein according to customary practice, the methionine corresponding to the translation initiation site is assigned to 1, i.e., the first amino acid. Therefore, in the case of the sequence of a mature protein in which the signal peptide has been removed, the amino acid numbers are decreased by the number of the amino acids of the signal peptide.

In the specification, an amino acid residue at a mutation site (an amino acid residue to be substituted with another amino acid) is expressed in a combination of the above-described single letter representing the kind of the amino acid residue and the figure representing the position of the amino acid residue. For example, if proline at position 428 is a mutation site, then the amino acid is designated as "G428."

1. Modified Lipases

A first aspect of the present invention is directed to a modified lipase (modified enzyme). The modified enzyme of the present invention has an amino acid sequence with a substitution made in the amino acid sequence of a *Candida cylindracea* derived lipase, wherein the substitution is:

(1) a substitution of asparagine for an amino acid corresponding to the amino acid at position 428 in the amino acid sequence set forth in SEQ ID NO: 1; or (2) a substitution of phenylalanine, methionine, or isoleucine for an amino acid corresponding to the amino acid at position 429 in the amino acid sequence set forth in SEQ ID NO: 1.

The sequence of SEQ ID NO: 1 is the amino acid sequence of a *Candida cylindracea* derived lipase LIP1, which comprises the signal peptide. In the substitution represented in (1), an amino acid corresponding to the amino acid at position 428 in this amino acid sequence is a target to be substituted with a given amino acid and is substituted with asparagine, resulting in an alteration of the substrate specificity of the lipase. In the substitution represented in (2), an amino acid corresponding to the amino acid at position 429 in the sequence of SEQ ID NO: 1 is a target to be substituted with a given amino acid and is substituted with phenylalanine, methionine, or isoleucine, resulting in an alteration of the substrate specificity of the lipase. Lipases after these amino acid substitutions, i.e., modified enzymes have an increased specificity for short-chain to medium-chain fatty acids ($C_4$ to $C_8$ fatty acids), and when allowed to act on milk fat, typically give a composition of the released fatty acids that is similar to that of a calf sublingual gland derived lipase. Preferably, these modified enzymes work well on short-chain fatty acids ($C_4$ to $C_6$ fatty acids), and best on $C_4$ fatty acid.

Herein, the term "corresponding" when used for an amino acid residue in the present specification means contributing equally to exhibition of functions among proteins (enzymes) being compared. For example, when an amino acid sequence for comparison to the base amino acid sequence (that is, the amino acid sequence set forth in SEQ ID NO: 1) is aligned while considering partial homology of the primary structure (that is, an amino acid sequence) so that the most appropriate comparison can be achieved (in this event, the alignment may be optimized by introducing gaps if necessary), an amino acid located at a position corresponding to a specific amino acid in the base amino acid sequence can be specified as a "corresponding amino acid". The "corresponding amino acid" can also be specified by comparison between conformations (three-dimensional structures) in place of or in addition to the comparison between primary structures. Utilization of conformational information can give highly credible comparison results. In this case, a technique of performing an alignment with comparing atomic coordinates of conformations of a plurality of enzymes can be adopted.

Conformational information of an enzyme to be mutated is available from, for example, the Protein Data Bank Japan.

One example of a method for determination of a protein conformation by the X-ray crystal structure analysis will be shown below.

(1) A protein is crystallized. Crystallization is essential to determine a conformation, and in addition, crystallization is industrially useful as a purification method of a protein at high purity and a stable preservation method of a protein at high density. In this case, a protein to which a substrate as a ligand or its analogous compound is bound may be preferably used for crystallization.

(2) The prepared crystal is irradiated with X ray to collect diffraction data. There are many cases that a protein crystal is damaged due to X ray irradiation and the diffraction ability is deteriorated. In such cases, a low-temperature measurement technique of rapidly cooling the crystal to about −173° C. and collecting diffraction data in the state has been recently prevailed. In addition, ultimately, synchrotron orbit radiation having high luminance is utilized to collect high resolution data that is used for structural determination.

(3) In addition to the diffraction data, phase information is necessary in order to perform the crystal structure analysis. When a crystal structure of an analogous protein to a desired protein is unknown, it is impossible to determine the structure in a molecular substitution method, and a phase problem has to be solved by a heavy-atom isomorphous replacement method. The heavy-atom isomorphous replacement method is a method in which a metallic atom having a high atomic number such as mercury or platinum is introduced into a crystal and contribution of a large X ray scattering ability of such a metallic atom to X ray diffraction data is utilized to collect phase information. The determined phase is possibly improved by smoothing an electron density of a solvent region in the crystal. Since a water molecule in the solvent region has large fluctuation, the electron density is hardly observed, and thus adjusting the electron density in this region to close to 0 makes it possible to approach the real electron density, which results in improving a phase. When plural molecules are contained in an asymmetrical unit, equation of electron densities of these molecules makes it possible to more significantly improve a phase. A model of a protein is fit to an electron density map calculated using the phase improved as described above. This process is performed on computer graphics using a program such as QUANTA made by MSI Co. (USA). After the process, structural precision is performed using a program such as X-PLOR made by MSI Co. to complete the structure analysis. When a crystal structure of an analogous protein to a desired protein is known, it can be determined in a molecular substitution method using the atomic coordinate of the known protein. Molecular substitution and structure refinement can be performed using a program such as CNS_SOLVE ver.11.

As *Candida cylindracea* derived lipases, there are known five enzymes (LIP1, LIP2, LIP3, LIP4, and LIP5). In addition, the applicant has found an enzyme (referred to as LIP1') that exhibits a high homology to LIP1, from lipase-producing mutant strains. For these six enzymes, the amino acid sequences without the signal peptide, i.e., the amino acid sequences of the mature enzymes are set forth in SEQ ID NOs: 2 (for LIP1), 3 (for LIP1'), 4 (for LIP2), 5 (for LIP3), 6 (for LIP4), and 7 (for LIP5). Typically, one of these enzymes will be used as a reference lipase (which is subjected to amino acids substitutions, resulting in the generation of modified enzymes). Therefore, specific examples of the amino acid sequence of a reference lipase are the amino acid sequences of SEQ ID NOs: 2 to 7. The identity to the amino acid sequence of *Candida cylindracea* derived lipase LIP1 (SEQ ID NO: 2) is 99% for the amino acid sequence of SEQ ID NO: 3, 79% for the amino acid sequence of SEQ ID NO: 4, 88% for the amino acid sequence of SEQ ID NO: 5, 81% for the amino acid sequence of SEQ ID NO: 6, and 82% for the amino acid sequence of SEQ ID NO: 7 (FIGS. 3 to 5).

For the substitution represented in (1) (a substitution for an amino acid corresponding to the amino acid at position 428 in the amino acid sequence of SEQ ID NO: 1), an enzyme consisting of an amino acid sequence 70% or more identical to the amino acid sequence of SEQ ID NO: 2 may be used as a reference lipase. For example, any of LIP1, LIP1', LIP2, LIP3, LIP4, and LIP5 can be the reference lipase. As a reference lipase, use is preferably made of an enzyme that has an amino acid sequence having 80% or more identity to the amino acid sequence of SEQ ID NO: 2 (with the proviso that the enzyme exhibits lipase activity), more preferably an enzyme that has an amino acid sequence having 90% or more identity to the amino acid sequence of SEQ ID NO: 2 (with the proviso that the enzyme exhibits lipase activity), even more preferably an enzyme that has an amino acid sequence having 95% or more identity to the amino acid sequence of SEQ ID NO: 2 (with the proviso that the enzyme exhibits lipase activity), and most preferably an enzyme that has an amino acid sequence having 99% or more identity to the amino acid sequence of SEQ ID NO: 2 (with the proviso that the enzyme exhibits lipase activity).

In LIP1 having the amino acid sequence of SEQ ID NO: 2, the amino acid corresponding to the amino acid at position 428 in the amino acid sequence of SEQ ID NO: 1 is leucine (L) at position 413. Therefore, when LIP1 having the amino acid sequence of SEQ ID NO: 2 is used as a reference lipase, this amino acid is a target to be substituted with a given amino acid. On the other hand, when LIP1' having the amino acid sequence of SEQ ID NO: 3 is used as a reference lipase, the amino acid to be substituted with a given amino acid is leucine (L) that is an amino acid located at position 413 in SEQ ID NO: 3. When LIP2 having the amino acid sequence of SEQ ID NO: 4 is used as a reference lipase, the amino acid to be substituted with a given amino acid is leucine (L) that is an amino acid located at position 413 in the amino acid sequence of SEQ ID NO: 4. When LIP3 having the amino acid sequence of SEQ ID NO: 5 is used as a reference lipase, the amino acid to be substituted with a given amino acid is leucine (L) that is an amino acid located at position 413 in SEQ ID NO: 5. When LIP4 having the amino acid sequence of SEQ ID NO: 6 is used as a reference lipase, the amino acid to be substituted with a given amino acid is leucine (L) that is an amino acid located at position 413 in the amino acid sequence of SEQ ID NO: 6. When LIP5 having the amino acid sequence of SEQ ID NO: 7 is used as a reference lipase, the amino acid to be substituted with a given amino acid is leucine (L) that is an amino acid located at position 413 in the amino acid sequence of SEQ ID NO: 7.

In the meanwhile, for the substitution represented in (2) (a substitution for an amino acid corresponding to the amino acid at position 429 in the amino acid sequence of SEQ ID NO: 1), an enzyme consisting of an amino acid sequence 90% or more identical to the amino acid sequence of SEQ ID NO: 2 may be used as a reference lipase. For example, any of LIP1 and LIP1' can be the reference lipase. As a reference lipase, use is preferably made of an enzyme that has an amino acid sequence having 95% or more identity to the amino acid sequence of SEQ ID NO: 2 (with the proviso that the enzyme exhibits lipase activity), more preferably an enzyme that has an amino acid sequence having 98% or more identity to the amino acid sequence of SEQ ID NO: 2 (with the proviso that the enzyme exhibits lipase activity), and most preferably an enzyme that has an amino acid sequence having 99% or more identity to the amino acid sequence of SEQ ID NO: 2 (with the proviso that the enzyme exhibits lipase activity).

In LIP1 having the amino acid sequence of SEQ ID NO: 2, the amino acid corresponding to the amino acid at position 429 in the amino acid sequence of SEQ ID NO: 1 is glycine (G) at position 414. Therefore, when LIP1 having the amino acid sequence of SEQ ID NO: 2 is used as a reference lipase, this amino acid is a target to be substituted with a given amino acid. On the other hand, when LIP1' having the amino acid sequence of SEQ ID NO: 3 is used as a reference lipase, the amino acid to be substituted with a given amino acid is glycine (G) that is an amino acid located at position 414 in SEQ ID NO: 3.

Here, specific examples of the amino acid sequences of modified enzymes are represented in SEQ ID NOs: 8 to 11. A modified enzyme having the amino acid sequence of SEQ ID NO: 8 (variant 1) is obtained by making a substitution of asparagine for an amino acid at position 413 on LIP1 having the amino acid sequence of SEQ ID NO: 2 (that is, a substitution represented in (1)); a modified enzyme having the amino acid sequence of SEQ ID NO: 9 (variant 2) is obtained by making a substitution of phenylalanine for an amino acid at position 414 on LIP1 having the amino acid sequence of SEQ ID NO: 2 (that is, one of the substitution represented in (2)); a modified enzyme having the amino acid sequence of SEQ ID NO: 10 (variant 3) is obtained by making a substitution of methionine for an amino acid at position 414 on LIP1 having the amino acid sequence of SEQ ID NO: 2 (that is, one of the substitution represented in (2)); and a modified enzyme having the amino acid sequence of SEQ ID NO: 11 (variant 4) is obtained by making a substitution of isoleucine for an amino acid at position 414 on LIP1 having the amino acid sequence of SEQ ID NO: 2 (that is, one of the substitution represented in (2)).

In cases where a portion of the amino acid sequence of a given protein has been subjected to mutagenesis, a mutated version of the protein may have a function equivalent to the original unmutated protein. That is, it is sometimes observed that a mutation in a given amino acid sequence does not lead to substantial effects on the function of the protein, which is maintained between before and after introducing the mutation. Taking this common general technical knowledge into account, it can be considered that when compared to an above-described modified enzyme (any of variants 1 to 4), a modified enzyme which has a slight difference in the amino acid sequence (wherein the difference in the amino acid sequence is located at a position(s) other than the position at which the above-described amino acid substitution has been performed), but which nevertheless does not have substantial differences in properties is an enzyme that is substantially the same as the above-described modified enzyme. The "slight difference in the amino acid sequence" in this context typically refers to the occurrence of a mutation(s) (change(s)) in the amino acid sequence resulting from deletion or substitution of one to several amino acids (for example, up to three, five, seven, or ten amino acids) contained in the amino acid sequence, or addition or insertion of one to several amino acids (for example, up to three, five, seven, or ten amino acids), or combinations thereof. The identity (%) between the amino acid sequences of "an enzyme that is substantially the same" and an above-described modified enzyme that is used as the reference is, for example, 90% or more, preferably 95% or more, more preferably 98% or more, most preferably 99% or more. Differences in the amino acid sequence may occur at more than one position. A "slight difference in the amino acid sequence" preferably results from conservative amino acid substitution.

2. Nucleic Acid Coding for Modified Lipase, Etc.)

The second aspect of the present invention provides a nucleic acid relating to the modified enzyme of the invention. That is, provided are a gene coding for the modified enzyme, a nucleic acid that can be used as a probe for identifying a nucleic acid coding for the modified enzyme, and a nucleic acid that can be used as a primer for amplifying or mutating a nucleic acid coding for the modified enzyme.

The gene coding for a modified enzyme is typically used in preparation of the modified enzyme. According to a genetic engineering procedure using the gene coding for a modified enzyme, a modified enzyme in a more homogeneous state can be obtained. Further, the method can be a preferable method also in the case of preparing a large amount of a modified enzyme. Note that uses of the gene coding for a modified enzyme are not limited to preparation of a modified enzyme. For example, the nucleic acid can also be used as a tool for an experiment intended for clarification of action mechanisms of a modified enzyme or a tool for designing or preparing a further modified form of an enzyme.

The "gene coding for a modified enzyme" herein refers to a nucleic acid capable of obtaining the modified enzyme when it is expressed, and includes, as a matter of course of a nucleic acid having a base sequence corresponding to the amino acid sequence of the modified enzyme, also a nucleic acid obtained by adding a sequence that does not code for an amino acid sequence to such a nucleic acid. Degeneracy of a codon is also considered.

Examples of the (base) sequence of the gene encoding a modified enzyme are represented in SEQ ID NOs: 12 to 15. These sequences encode variants described in the Examples section which follows, as indicated below.

SEQ ID NO: 12: variant 1 (L428N)
SEQ ID NO: 13: variant 2 (G429F)
SEQ ID NO: 14: variant 3 (G429M)
SEQ ID NO: 15: variant 4 (G429I)

In *Candida cylindracea*, the CTG codon encodes serine. If a gene is recombinantly expressed using other yeasts and the like as a host, then it is necessary that depending on the host to be used, the CTG codon is changed to another codon encoding serine (TCT, TCC, TCA, ATG, or AGC). The present invention also provides, as the sequence of a gene for use in heterologous expression, a sequence in which a codon substitution of this type is made for the sequence of any one of SEQ ID NOs: 12 to 15. Examples of sequences with a codon substitution are as follows.

SEQ ID NO: 16, which is a sequence with a codon substitution in the sequence of SEQ ID NO: 12;
SEQ ID NO: 17, which is a sequence with a codon substitution in the sequence of SEQ ID NO: 13;
SEQ ID NO: 18, which is a sequence with a codon substitution in the sequence of SEQ ID NO: 14; and
SEQ ID NO: 19, which is a sequence with a codon substitution in the sequence of SEQ ID NO: 15.

When a gene according to the present invention is to be expressed in a host, the gene will usually be inserted into the host in the form of a gene construct in which the above-described sequence has a signal peptide-coding sequence (a signal sequence) added thereto at the 5' end. The signal sequence of wild-type LIP1 is represented in SEQ ID NO: 21. The amino acid sequence encoded by this signal sequence (that is, the signal peptide) is represented in SEQ ID NO: 22. The signal sequence may be selected depending on the host to be used. Any signal sequence that can express a variant of interest can be used in the present invention. Examples of the signal sequence that can be used in the present invention can be illustrated by the following: a sequence encoding the signal peptide of the α-factor (Protein Engineering, 1996, vol. 9, p. 1055-1061), a sequence encoding the signal peptide of the α-factor receptor, a sequence encoding the signal peptide of the SUC2 protein, a sequence encoding the signal peptide of the PHOS protein, a sequence encoding the signal peptide of the BGL2 protein, a sequence encoding the signal peptide of the AGA2 protein, a sequence encoding the signal peptide of TorA (trimethylamine N-oxidoreductase), a sequence encoding the signal peptide of *Bacillus subtilis* derived PhoD (phosphoesterase), a sequence encoding the signal peptide of *Bacillus subtilis* derived LipA (lipase), a sequence encoding the signal peptide of *Aspergillus oryzae* derived Taka-amylase (JP 2009-60804 A), a sequence encoding the signal peptide of *Bacillus amyloliquefaciens* derived α-amylase (Eur. J. Biochem. 155, 577-581 (1986)), a sequence encoding the signal peptide of *Bacillus subtilis* derived neutral protease (APPLIED AND ENVIRONMENTAL MICROBIOLOGY, April 1995, p. 1610-1613, Vol. 61, No. 4), and a sequence encoding the signal peptide of *Bacillus* derived cellulase (JP 2007-130012 A).

The nucleic acid of the present invention can be prepared in an isolated state by use of a standard genetic engineering technique, molecular biological technique, biochemical technique, and the like in reference to the present specification or the sequence information disclosed in the appended sequence listing.

Another embodiment of the present invention provides a nucleic acid different in a base sequence in a part (hereinafter also referred to as a "homologous nucleic acid", and a base sequence defining a homologous nucleic acid is also referred to as a "homologous base sequence") as compared to the base sequence of the gene coding for the modified enzyme of the invention, although functions of a protein coded by the nucleic acid are equal. An example of the homologous nucleic acid includes a DNA composed of a base sequence containing substitution, deletion, insertion, addition or inversion of 1 to several bases on the basis of the base sequence of the nucleic acid coding for the modified enzyme of the present invention and coding for a protein having activity which is characteristic to the modified enzyme (i.e. lipase activity). Substitution or deletion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases.

Such a homologous nucleic acid as described above can be obtained by, for example, a restriction enzyme treatment, a treatment with exonuclease, DNA ligase, etc., and introduction of mutation by a site directed mutation introduction method (Molecular Cloning, Third Edition, Chapter 13, Cold Spring Harbor Laboratory Press, New York), and random mutation introduction method (Molecular Cloning, Third Edition, Chapter 13, Cold Spring Harbor Laboratory Press, New York). The homologous nucleic acid can be obtained also in other methods such as exposure to ultraviolet radiation.

Another embodiment of the present invention relates to a nucleic acid having a base sequence complementary to the base sequence of the gene coding for the modified enzyme of the invention. Another embodiment of the present invention provides a nucleic acid having a base sequence with an identity of at least about 60%, 70%, 80%, 90%, 95%, 99%, or 99.9% to the base sequence of the gene coding for the modified enzyme of the invention or a base sequence complementary to the base sequence.

Another embodiment of the present invention relates to a nucleic acid having a base sequence hybridizing to a base sequence complementary to the base sequence of the gene coding for the modified enzyme of the invention or its homologous base sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization liquid (50% formamide, 10×SSC (0.15 M NaCl, 15 mM sodium citrate, pH 7.0), a 5×Denhardt solution, 1% SDS, 10% dextran sulfate, 10 µg/ml of modified salmon sperm DNA, and a 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), a 1×Denhardt solution, 1% SDS, 10% dextran sulfate, 10 µg/ml of modified salmon sperm DNA, and a 50 mM phosphate buffer (pH 7.5) as a hybridization liquid.

Another embodiment of the present invention provides a nucleic acid (nucleic acid fragment) having a part of the base sequence of the gene coding for the modified enzyme of the invention or a base sequence complementary to the base sequence. Such a nucleic acid fragment can be used in detection, identification, and/or amplification of a nucleic acid having the base sequence of the gene coding for the modified enzyme of the present invention. For example, the nucleic acid fragment is designed so as to at least contain a part being hybridized to a sequential nucleotide moiety (for example, about 10 to about 100 bases length, preferably about 20 to about 100 bases length, more preferably about 30 to about 100 bases length) in the base sequence of the gene coding for the modified enzyme of the invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for a modified enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed in a standard recombinant DNA technique (for example, a known method of using a restriction enzyme and a DNA ligase, which can be referred in Molecular Cloning, Third Edition, 1.84, Cold Spring Harbor Laboratory Press, New York).

As host cells, there can be employed, for example, microbial cells of koji mold (for example, *Aspergillus oryzae*), bacilli (for example, *Bacillus subtilis*), *Escherichia coli*, and *Saccharomyces cerevisiae*, in terms of easy handling; however, any host cell in which a recombinant DNA can be replicated and a gene encoding a modified enzyme can be expressed can be utilized. Preferably, *Escherichia coli* and *Saccharomyces cerevisiae* can be employed as a host organism. *Candida* yeasts such as *Candida cylindracea* can also be used as a host organism. In addition, *Pichia* yeasts such as *Pichia pastoris* can also be used as a host organism.

Strains of *Escherichia coli* can be *Escherichia coli* strain BL21(DE3)pLysS in cases of using a T7-based promoter, and *Escherichia coli* strain JM109 in other cases. Strains of *Saccharomyces cerevisiae* can be *Saccharomyces cerevisiae* strain SHY2, AH22, or INVSc1 (Invitrogen).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, electroporation (Potter, H. et al., Proc. Natl. Acad. Sci. U.S.A. 81, 7161-7165 (1984)), and lipofectin (Feigner, P. L. et al., Proc. Natl. Acad. Sci. U.S.A. 84, 7413-7417 (1984)). The microorganism of the present invention can be used for producing the modified enzyme of the invention.

3. Enzyme Preparation Containing Modified Lipase

The modified enzyme of the present invention is provided, for example, in the form of an enzyme preparation. The enzyme preparation may contain an excipient, a buffer agent, a suspending agent, a stabilizer, a preservative, an antiseptic, saline and the like besides the active ingredient (the modified enzyme of the present invention). As the excipient, starch, dextrin, maltose, trehalose, lactose, D-glucose, sorbitol, D-mannitol, white soft sugar, glycerol and the like can be used. As the buffer agent, phosphates, citrates, acetates and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, ethanol, benzalkonium chloride, paraoxybenzoic acid, chlorobutanol and the like can be used.

4. Uses of Modified Lipases

A further aspect of the present invention is directed to uses of modified enzymes and enzyme preparations. A modified enzyme according to the present invention has a substrate specificity similar to that of an animal lipase, that is, a selectivity for short-chain to medium-chain fatty acids. Taking advantage of this property, the present invention utilizes such a modified enzyme or a preparation thereof for flavor improvement of food products or food raw materials. "Flavor improvement" refers to providing a given product or raw material with a more favorable flavor than its original flavor (that is, the flavor of the given product or raw material to which the present invention is not applied) by increasing or adding its particular flavor component(s). Typically, flavor improvement results in the enhancement of a flavor characteristic of a given food product or food raw material. The flavor may be improved by masking an unfavorable flavor component(s).

Food products or food raw materials to which the present invention can be applied can be illustrated by the following: dairy products, margarine-based products (margarines, fat spreads), shortenings, ice cream-based products (ice creams, gelati, frozen yogurts, sundaes, smoothies, soft creams, etc.), ices, mousses, Bavarian creams, snacks, dressings, soups, various vegetable oils (soybean oil, rapeseed oil, corn oil, palm oil, palm kernel oil, coconut oil, sunflower oil, cottonseed oil, etc.).

For example, by allowing a modified enzyme or enzyme preparation of the present invention to act on a food product or food raw material, its flavor can be improved. On the other hand, if a modified enzyme or enzyme preparation of the present invention is added to or mixed to a raw material or intermediate product in a step for producing the food product, then a food product with an improved flavor can be produced. Alternatively, the flavor of a food product or food raw material may be improved, for example, by addition or mixing of a composition that is obtained using a modified enzyme or enzyme preparation of the present invention.

A modified enzyme or enzyme preparation of the present invention is suitable particularly for the production of dairy products. The flavor of dairy products, particularly the cheese flavor, can be increased or improved by applying to them a modified enzyme or enzyme preparation of the present invention.

Examples of dairy products to which a modified enzyme or enzyme preparation of the present invention can be applied can include various types of cheese (Cheshire cheese, Cheddar cheese, Edam cheese, Gouda cheese, Emmental cheese, Parmesan cheese, Pecorino cheese, etc.), processed cheese (process cheese), EMC (Enzyme modified cheese), cheese foods (which are produced by processing one or more kinds of natural or process cheese and have a cheese weight of 51% or higher in the product), butters, yogurts, creams, spreads, modified milk powders, and seasonings (to be used, for example, for snacks, dressings, and soups). Milks that are used as the main raw material for dairy products are ones from cows, sheep, goats, and others.

A modified enzyme or enzyme preparation of the present invention is added, for example, to a raw material or intermediate product during the course of producing the food product. This allows the enzyme to act on the milk fat present in the raw material or intermediate product, thereby leading to the release of fatty acids. The modified enzyme or enzyme preparation of the present invention can be added at various stages in the course of producing the dairy product. Amounts (concentrations) of enzyme to be used, temperature conditions, reaction time, and others may be determined through preliminary experiments.

EXAMPLES

A. Generation of New Lipases

The inventors carried out the investigation described below, with aiming at the generation of new lipases.

1. Objectives and Investigation Strategy

The inventors made investigations, paying attention to:

(1) Aiming at acquiring a microbial lipase that provides a similar composition of released fatty acids to that provided by a calf sublingual gland derived lipase when the microbial lipase is allowed to act on cheese. In particular, attempts were made to change the fatty acid specificity from long-chain to short-chain fatty acids.

(2) Making the substrate pocket of an enzyme protein small, thereby to change the substrate specificity.

(3) Replacing an amino acid in the substrate pocket with a more bulky amino acid, thereby to making the substrate pocket smaller.

2. Methods (1) Selection of Mutation Sites

Amino acids that interact with substrates were selected based on the sequence of *Candida cylindracea* derived lipase LIP1 (its amino acid sequence including the signal peptide is represented in SEQ ID NO: 1, and the sequence of the gene encoding the amino acid sequence in SEQ ID NO: 20, and the amino acid sequence of the mature lipase without the signal peptide in SEQ ID NO: 2) and on the three dimensional structures deposited in public databases. Specifically, proline at position 261 (P261), leucine at position 319 (L319), and leucine at position 428 (L428) were selected. These amino acid residues correspond to P246, L304, and L413, respectively, in the literature by Schmitt et al. (Non Patent Document 1: J. Schmitt et al., Protein Engineering, vol. 15, no. 7, pp. 595-601, 2002).

At the same time, mutation sites were searched by computer analysis with taking note of the increase of the hydrophobicity in the pocket to improve the ability to synthesize esters. Serine at position 380 (S380) and glycine at position 429 (G429), which are neutral amino acids, were selected.

(2) Acquirement of DNA Sequences Encoding Mutated Amino Acid Sequences

A *Pichia pastoris* host expression system (Invitrogen, *Pichia* Expression Kit) was used. As a plasmid, pPIC3.5k was used. The gene for *Candida cylindracea* derived LIP1 that was used as a template was an LIP1-encoding sequence codon-optimized for *Saccharomyces cerevisiae*. Mutations were introduced by Inverse PCR method (TOYOBO, KOD-Plus-Mutagenesis Kit), thereby preparing genes encoding various variants with an amino acid substitution occurring at selected sites for mutation. A plasmid carrying a mutated LIP1 gene was transformed into *E. coli* strain DH5α. Subsequently, the plasmid carrying the mutated LIP1 gene was extracted from transformed *E. coli* cells.

(3) Acquirement of Transformants Expressing Mutated Amino Acid Sequences

The plasmid carrying the mutated LIP1 gene was transformed into *Pichia pastoris* strain GS 115 (Invitrogen, *Pichia* Expression Kit). A resulting *Pichia pastoris* transformant was cultured and the enzyme (variant lipase) was collected form the cultured supernatant.

(4) Decomposition of Milk Fat Using Variant Lipases

As a substrate, natural cheese (young Cheddar cheese) was used which was suspended and dispersed in phosphate buffer (pH 6.8) at a weight ratio of 1:1. The reaction was carried out under conditions at 50° C. for 16 hours. The amount of each variant lipase to be added was 0.1 mg protein per 1 g of cheese. After the reaction was completed, the released fatty acids in the cheese were extracted with diethyl ether and subjected to gas chromatography.

Figure 2:
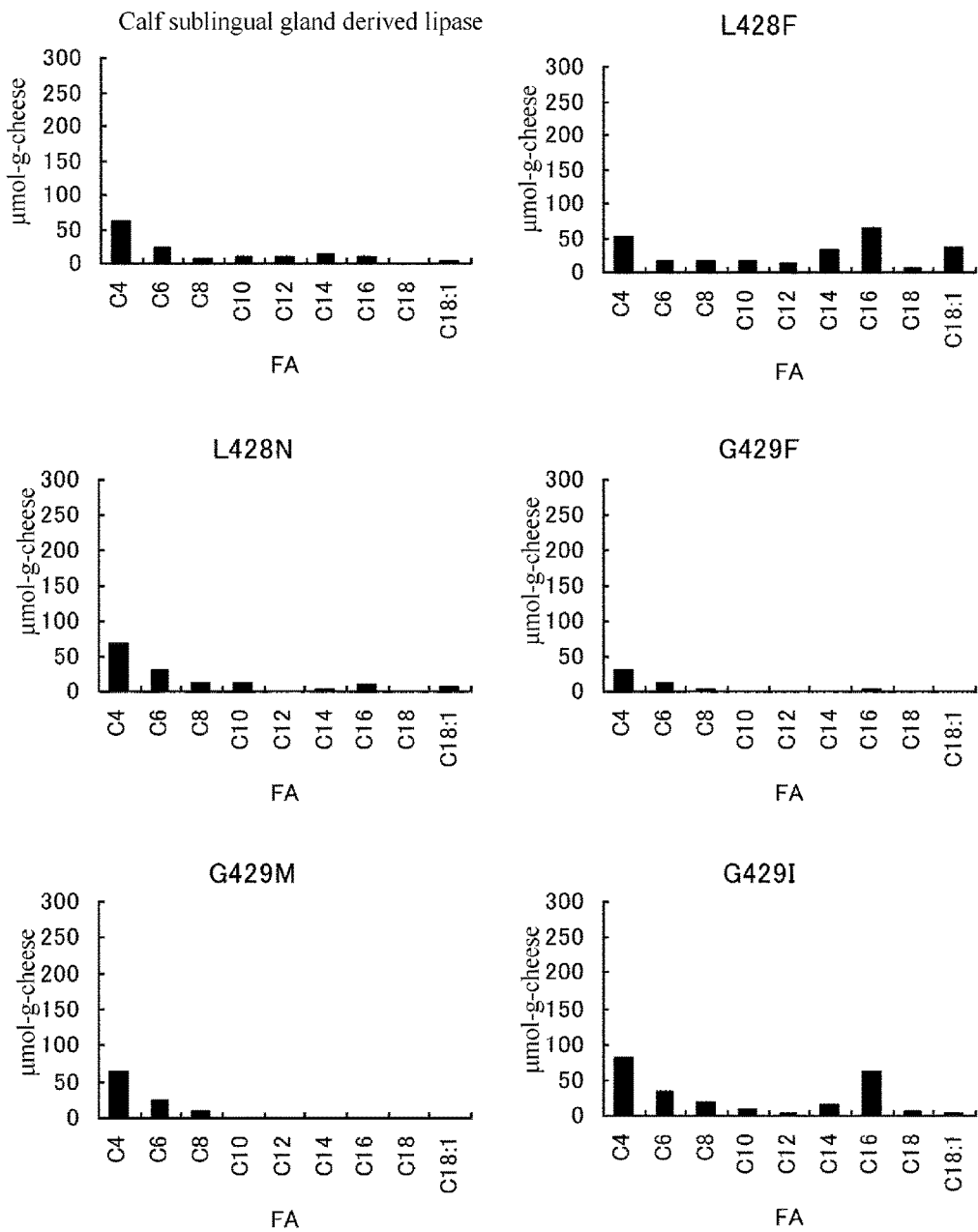
FIG. 2 shows the composition of released fatty acids after treatment with modified enzymes. Various modified lipases (variants) were allowed to act on cheese (used as a substrate) and a comparison was made for the compositions of the released fatty acids. The upper left panel shows results when a calf sublingual gland derived lipase was used. The lower panels show results when modified lipases were used (variant 1: L428N; variant 2: G429F, variant 3: G429M; and variant 4: G429I). The upper right panel shows results when a modified lipase (L428F) that had previously been reported was used.

From the results of evaluation on more than ten variant lipases, it was found that several of the variant lipases gave a composition of the released fatty acids that, unlike that in the case of a wild-type lipase (FIG. 1), was similar to that in the case of a calf sublingual gland derived lipase (variant 1: L428N, variant 2: G429F, variant 3: G429M, and variant 4: G429I; FIG. 2). Accordingly, the inventors have succeeded in obtaining variant lipases that selectively release short-chain to medium-chain fatty acids ($C_4$ to $C_8$ fatty acids). When allowed to act on milk fat, these variant lipases work well on short-chain fatty acids ($C_4$ to $C_6$ fatty acids), and best on $C_4$ fatty acid. Among these variant lipases, variant 3 is remarkable in that it is more specific for short-chain fatty acids than the calf sublingual gland derived lipase. For comparison, the result for the variant L428F reported in the above-mentioned literature (which is referred to therein as L413F) is shown (FIG. 2, upper right panel). Variant L428F releases long-chain fatty acids in relatively large amounts. The amino acid sequences of these variants and the sequences of the genes encoding them (wherein codons characteristic of *Candida* yeasts are used so as to correspond to wild type lipase) are as follows:

<Variant 1>
  Amino acid sequence: SEQ ID NO: 8
  Gene sequence: SEQ ID NO: 12

<Variant 2>
  Amino acid sequence: SEQ ID NO: 9
  Gene sequence: SEQ ID NO: 13
<Variant 3>
  Amino acid sequence: SEQ ID NO: 10
  Gene sequence: SEQ ID NO: 14
<Variant 4>
  Amino acid sequence: SEQ ID NO: 11
  Gene sequence: SEQ ID NO: 15

B. Expression of a Variant Lipase in Various Hosts (1) Expression of a Variant Lipase in *Escherichia coli*

A gene for a variant lipase (G429M) was inserted into a plasmid pET20b. The variant lipase was expressed using *Escherichia coli* Origami B (DE3) as a host. A resulting transformant was cultured under conditions at 15° C. for 40 hours to obtain bacterial cells. The bacterial cells were disrupted with a Bead Shocker, and lipase activity of the resultant extract was measured. For measuring the lipase activity for short-chain fatty acids, a Lipase Kit S (DS Biopharma Medical) was used. For measuring the lipase activity for long-chain fatty acids, a fat-digesting capacity LMAP method was used. The results revealed that the lipase activity of the cell extract was 1.85 u/mL when the Lipase Kit S was used and 0 u/mL when the LMAP method was used.

A gene for a variant lipase (G429M) was inserted into a plasmid pCold-TF. The variant lipase was expressed using *Escherichia coli* Origami B (DE3) as a host. A resulting transformant was cultured in LB medium under conditions at 15° C. for 40 hours to obtain bacterial cells. The bacterial cells were disrupted with a Bead Shocker, and lipase activity of the resultant extract was measured. The results revealed that the lipase activity of the cell extract was 3.95 u/mL when the Lipase Kit S was used and 0 u/mL when the LMAP method was used.

As mentioned above, a variant lipase (G429M) specific for short-chain fatty acids was able to be expressed.

(2) Expression of a Variant Lipase in a Yeast (*Candida cylindracea*) Strain

A variant lipase (G429M) was expressed using as a host a strain of *Candida cylindracea* that had been made auxotrophic by mutagenesis. A resulting transformant was cultured under conditions at 25° C. for 48 hours, and lipase activity of the cultured supernatant was measured. For measuring the lipase activity for short-chain fatty acids, an FCCIII method was used. For measuring the lipase activity for long-chain fatty acids, a fat-digesting capacity LMAP method was used. The results revealed that the lipase activity of the cultured supernatant of the *Candida cylindracea* strain in which the variant lipase (G429M) was allowed to be expressed was 470 u/mL when the FCIII method was used and 155 u/mL when the LMAP method was used (a ratio of short-chain to long-chain fatty acids=3:1). For comparison, when a measurement was made of the lipase activity of the cultured supernatant of the parent host strain into which the variant lipase gene had been not introduced, the activity was 267 u/mL when the FCIII method was used and 599 u/mL when the LMAP method was used (a ratio of short-chain to long-chain fatty acids=2:5).

As mentioned above, a variant lipase (G429M) specific for short-chain fatty acids was able to be expressed.

(3) Expression of a Variant Lipase in a Filamentous Fungus (*Aspergillus oryzae*) Strain A variant lipase (G429M) was expressed using as a host a strain of *Aspergillus oryzae* that had been made auxotrophic by mutagenesis and by means of using an amylase promoter. A resulting transformant was cultured under conditions at 30° C. for 76 hours, and lipase activity of the cultured supernatant was measured. For measuring the lipase activity for short-chain fatty acids, an FCCIII method was used. For measuring the lipase activity for long-chain fatty acids, a fat-digesting capacity LMAP method was used. The results revealed that the lipase activity of the cultured supernatant of the *Aspergillus oryzae* strain in which the variant lipase (G429M) was allowed to be expressed was 39 u/mL when the FCIII method was used and 0 u/mL when the LMAP method was used.

As mentioned above, a variant lipase (G429M) specific for short-chain fatty acids was able to be expressed.

(4) Expression of a Variant Lipase in a *Bacillus subtilis* Strain

Into a plasmid pHY300PLK was inserted a variant lipase (G429M) gene having a pullulanase promoter added thereto. The variant lipase was expressed using a *Bacillus subtilis* strain as a host. Lipase activity of the cultured medium of a resulting transformant was measured. For measuring the lipase activity for short-chain fatty acids, a Lipase Kit S (DS Biopharma Medical) was used. For measuring the lipase activity for long-chain fatty acids, a fat-digesting capacity LMAP method was used. The results revealed that the lipase activity of the cultured medium was 0.3 u/mL (and 0.1 u/mL for a control strain transformed with an empty vector) when the Lipase Kit S was used and 0 u/mL when the LMAP method was used.

As mentioned above, a variant lipase (G429M) specific for short-chain fatty acids was able to be expressed.

INDUSTRIAL APPLICABILITY

The modified lipase according to the present invention exhibits specificity for short-chain to medium-chain fatty acids. The modified lipase according to the present invention has a great deal of potential, in particular, in the production of dairy products having a cheese flavor, such as cheeses or cheese products.

The present invention should not be limited in any way to the description of the embodiments and examples of the above-described invention. The present invention also includes a variety of modified embodiments within the scope that one skilled in the art could easily arrive without departing from the description of the scope of claims. The contents of articles, published patent applications, patent publications, and others that are expressly provided are incorporated in their entire content by citation.

The invention claimed is:

1. A modified lipase consisting of an amino acid sequence with a substitution made in the amino acid sequence of a *Candida cylindracea* derived lipase, wherein the substitution is:

(1) a substitution of asparagine for an amino acid corresponding to the amino acid at position 428 in the amino acid sequence set forth in SEQ ID NO: 1; or (2) a substitution of phenylalanine, methionine, or isoleucine for an amino acid corresponding to the amino acid at position 429 in the amino acid sequence set forth in SEQ ID NO:1, wherein the amino acid sequence of the *Candida cylindracea* derived lipase is an amino acid sequence that is 90% or more identical to the amino acid sequence of SEQ ID NO: 2 and wherein the substitution is the substitution represented in (1), or wherein the amino acid sequence of the *Candida cylindracea* derived lipase is an amino acid sequence that is 90% or more identical to the amino acid sequence of SEQ ID NO: 2 and wherein the substitution is the substitution represented in (2).

2. The modified lipase according to claim 1, wherein the amino acid sequence of the *Candida cylindracea* derived lipase is an amino acid sequence of SEQ ID No. 2.

3. The modified lipase according to claim 1, consisting of the amino sequence set forth in SEQ ID No. 10.

4. A gene encoding the modified lipase according to claim 1.

5. The gene according to claim 4, comprising the polynucleotide sequence set forth in SEQ ID No. 14.

6. A recombinant DNA comprising the gene according to claim 4.

7. A microorganism carrying the recombinant DNA according to claim 6.

8. The microorganism according to claim 7, wherein the host is *Escherichia coli, Candida cylindracea, Aspergillus oryzae, Bacillus subtilis,* or *Pichia pastoris.*

9. An enzyme preparation comprising the modified lipase according to claim 1.

10. A method for improving the flavor of a food product or food raw material, wherein the enzyme according to claim 1 is allowed to act on the food product or food raw material.

11. A method for producing a food product, wherein the enzyme according to claim 1 is allowed to act on a food raw material or intermediate product.

12. The method according to claim 10, wherein the food product is a dairy product.

13. A flavor-improving agent that is allowed to act on a food product or food raw material, comprising the enzyme according to claim 1 or the enzyme preparation according to claim 9.

14. A food product or food raw material obtained by treatment with the enzyme according to claim 1.

15. The method according to claim 11, wherein the food product is a dairy product.

* * * * *